(12) United States Patent
Ramakrishnan et al.

(10) Patent No.: US 10,016,417 B2
(45) Date of Patent: Jul. 10, 2018

(54) EXTENDED RELEASE FORMULATION OF A DIRECT THROMBIN INHIBITOR

(71) Applicant: Diakron Pharmaceuticals Inc., Morris Plains, NJ (US)

(72) Inventors: Sankar Ramakrishnan, Maddukkur (IN); Elumalal Venkatesan, Chennai (IN); Jayanthi Suryakumar, Hyderabad (IN); Stephane Allard, Englewood, NJ (US)

(73) Assignee: Diakron Pharmaceuticals, Inc., Morris Plains, NJ (US)

( * ) Notice: Subject to any disclaimer, the term of this patent is extended or adjusted under 35 U.S.C. 154(b) by 0 days.

(21) Appl. No.: 14/356,833

(22) PCT Filed: Nov. 6, 2012

(86) PCT No.: PCT/US2012/063734
§ 371 (c)(1),
(2) Date: May 7, 2014

(87) PCT Pub. No.: WO2013/070623
PCT Pub. Date: May 16, 2013

(65) Prior Publication Data
US 2014/0309239 A1     Oct. 16, 2014

Related U.S. Application Data

(60) Provisional application No. 61/556,771, filed on Nov. 7, 2011.

(51) Int. Cl.
*A61K 31/497*    (2006.01)
*A61K 9/20*    (2006.01)

(52) U.S. Cl.
CPC .......... *A61K 31/497* (2013.01); *A61K 9/2054* (2013.01)

(58) Field of Classification Search
USPC .................................................. 514/255.05
See application file for complete search history.

(56) References Cited

U.S. PATENT DOCUMENTS

| 6,277,863 | B1 | 8/2001 | Krantz et al. |
| 6,455,532 | B1 | 9/2002 | Burgey et al. |
| 6,521,625 | B2 | 2/2003 | Cowden et al. |
| 2004/0197404 | A1 | 10/2004 | Ellstrom et al. |
| 2004/0213850 | A1 | 10/2004 | Dokou et al. |
| 2006/0134198 | A1 | 6/2006 | Tawa et al. |
| 2009/0012115 | A1 | 1/2009 | Phillips et al. |
| 2011/0105753 | A1 | 5/2011 | Reddy et al. |

FOREIGN PATENT DOCUMENTS

WO    WO 2002/051402 A1    7/2002

OTHER PUBLICATIONS

Stangier, Joachim.: "Clinical Pharmacokinetics and Pharmacodynamics of the Oral Direct Thrombin Inhibitor Dabigatran Etexilate", Clinical Pharmacokinetics, vol. 47, No. 5, 2008, pp. 285-295, XP008173360.
Eriksson et al.: "Comparative Pharmacodynamics and Pharmacokinetics of Oral Direct Thrombin and Factor Xa Inhibitors in Development", Clinical Pharmacokinetics, vol. 48, No. 1, 2009, pp. 1-22, XP009153303.
International Search Report in corresponding International Application No. PCT/US2012/063734, dated Jan. 25, 2013.
Extended European Search report for PCT/US2012/63734, dated Jul. 8, 2015.
Euler et al. "Influence of physicochemical properties and intestinal region on the absorption of 3-fluoro-2-pyrimidylmethyl 3-(2,2-difluoro-2-(2-pyridyl)ethylamino)-6-chloropyrazin-2-one-1-acetamide, a water insoluble thrombin inhibitor, in dogs" International Journal of Pharmaceutics 275 (2004) 19-27.

*Primary Examiner* — Kathrien A Cruz
(74) *Attorney, Agent, or Firm* — Knobbe, Martens, Olson & Bear, LLP

(57) ABSTRACT

Extended release formulations of 3-fluoro-2-pyridylmethyl-3-(2,2-difluoro-2-(2-pyridyl)ethylamino)-6-chloropyrazin-2-one-1-acetamide (DPOC-4088) that provide for better control of blood plasma levels. The extended release formulations maintain substantially constant plasma levels of the active ingredient for at least about 16 hours and provide for once-daily dosing.

8 Claims, 17 Drawing Sheets

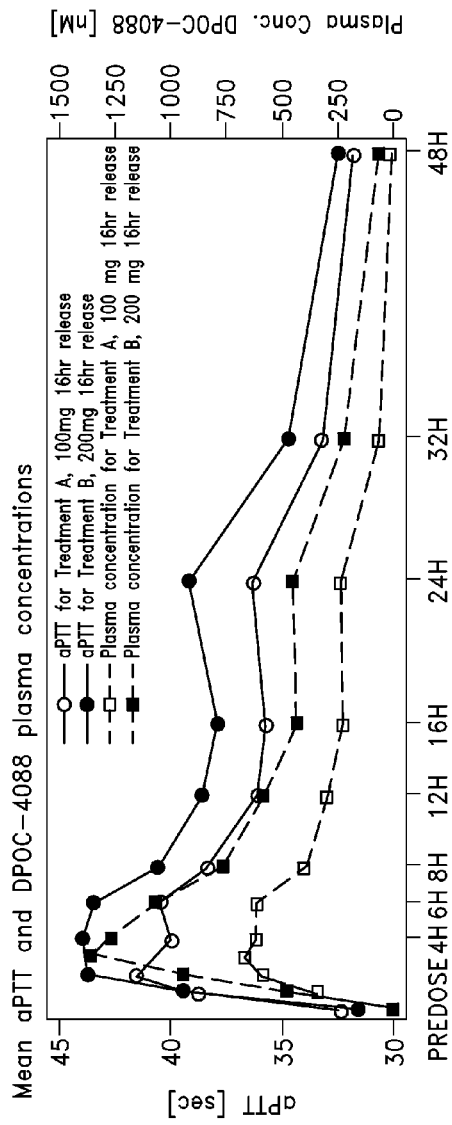
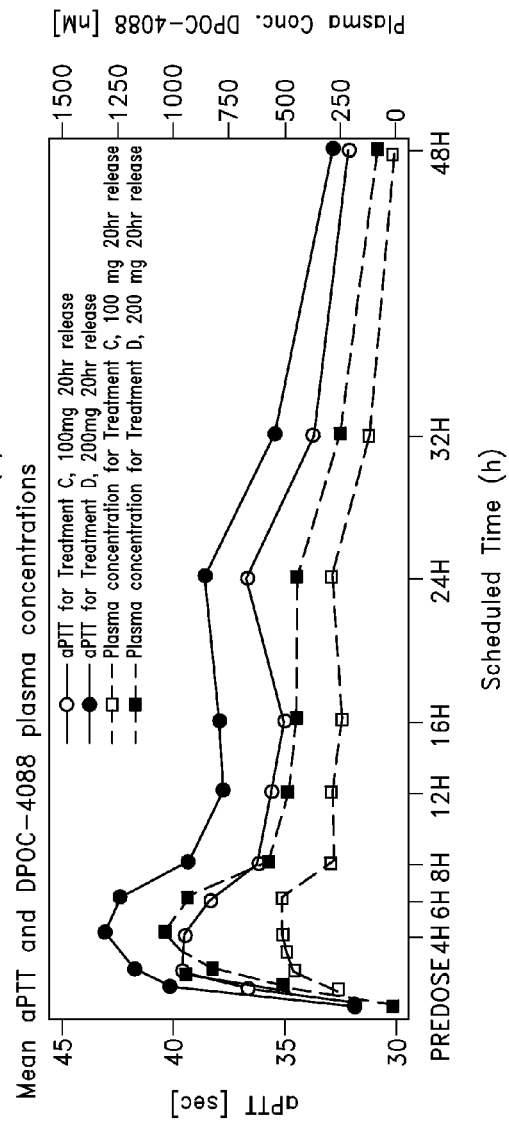
FIG. 10A
FIG. 10B

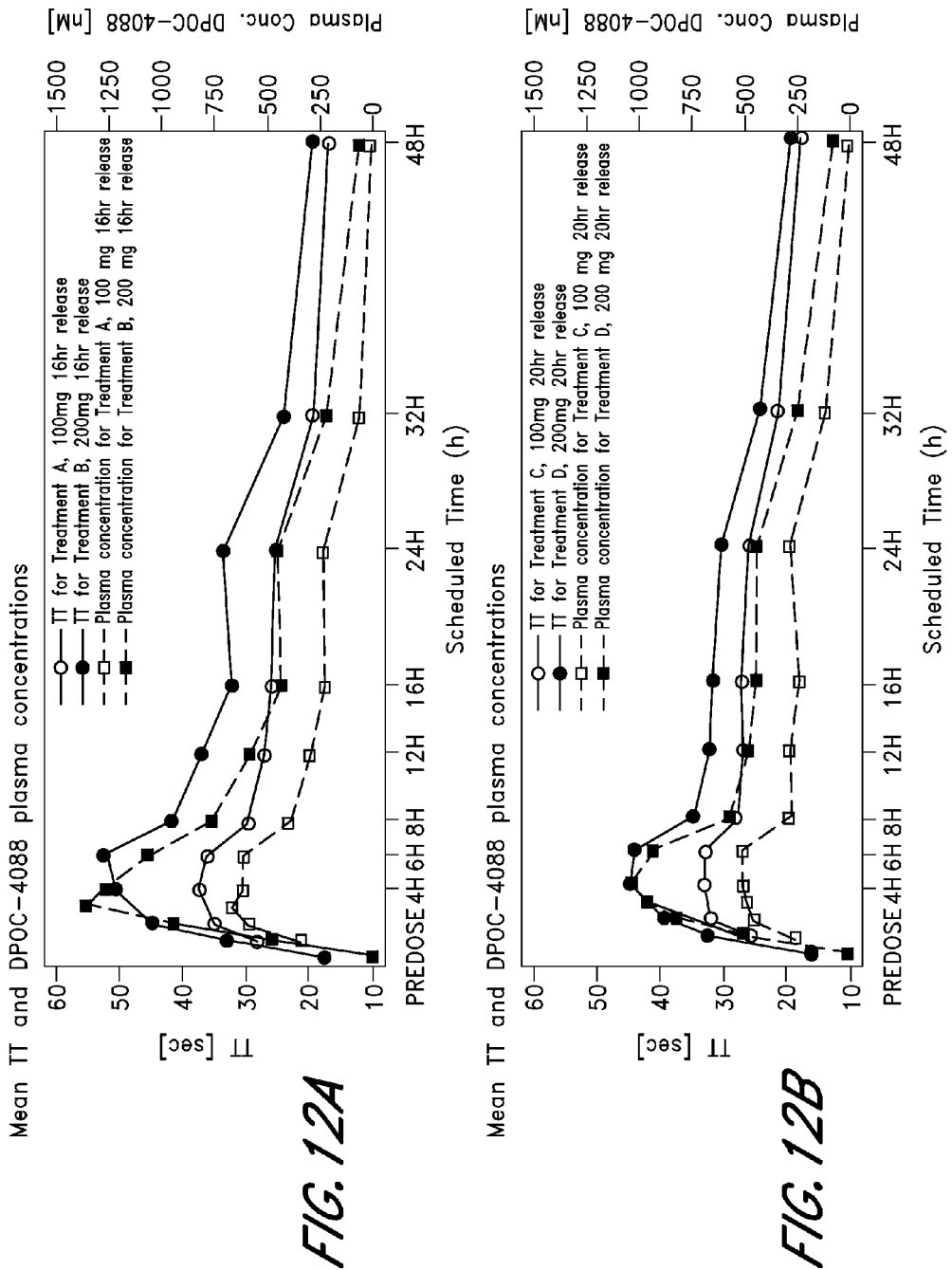

EXTENDED RELEASE FORMULATION OF A DIRECT THROMBIN INHIBITOR

This application is the U.S. National Phase under 35 U.S.C. § 371 of International Application PCT//US2012/063734, filed Nov. 6, 2012, designating the U.S., and published in English as WO 2013/070623 on May 16, 2013, which claims priority to U.S. Provisional Application No. 61/556,771, filed Nov. 7, 2011, the entire contents of which are incorporated herein by reference.

FIELD OF THE INVENTION

The present invention relates to extended release formulations for administering 3-fluoro-2-pyridylmethyl-3-(2,2-difluoro-2-(2-pyridyl)ethylamino)-6-chloropyrazin-2-one-1-acetamide that provide for better control of blood plasma levels. The extended release formulations maintain substantially constant plasma levels of the active ingredient for at least about 16 hours and provide for once-daily dosing.

BACKGROUND OF THE INVENTION

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thrombotic or thromboembolic disorders and include acute coronary syndrome, unstable angina, myocardial infarction, ischemic stroke, deep vein thrombosis, peripheral occlusive arterial disease, transient ischemic attack, and pulmonary embolism. In addition, thrombosis occurs on artificial surfaces in contact with blood, including catheters and artificial heart valves. Therefore, drugs that inhibit blood coagulation, or anticoagulants, are "pivotal agents for prevention and treatment of thromboembolic disorders" (Hirsch, J. et al. Blood 2005, 105, 453-463).

U.S. Pat. Nos. 6,455,532 and 6,521,625 disclose 3-fluoro-2-pyridylmethyl-3-(2,2-difluoro-2-(2-pyridyl)ethylamino)-6-chloropyrazin-2-one-1-acetamide (herein after referred to as DPOC-4088), which is an orally active, potent, rapidly binding, reversible, competitive, direct thrombin inhibitor suitable for prevention/treatment of venous and cardiogenic thromboembolism. With regard to anticoagulants that can be taken orally, warfarin has long been the standard. However, this compound has a narrow therapeutic window and possesses a significant risk of hemorrhage at therapeutic concentrations.

Therapeutic compounds meant for oral administration are generally administered as immediate release dosage forms which produce a sharp peak and subsequent relatively significant trough in plasma concentrations resulting in high peak to trough ratio or high degree of fluctuation. Such formulations may not provide sustained therapeutic action requiring multiple dosing and possess potential safety concerns for drugs not well tolerated at high levels.

Degree of Fluctuation ("DFL") is a measurement of how much plasma levels of a drug vary over the course of a dosing interval. The closer the DFL is to zero, the less is the variance in plasma levels of the drug over the course of a dosing period. Thus, a reduced DFL signifies that the difference in peak and trough plasma levels has been reduced.

U.S. Patent publication 2004/0213850 (the entirety of which is incorporated herein by reference) discloses a pharmaceutical composition comprising a tablet core comprising a therapeutically effective amount of 3-fluoro-2-pyridylmethyl-3-(2,2-difluoro-2-(2-pyridyl)ethylamino)-6-chloropyrazin-2-one-1-acetamide, or a pharmaceutically acceptable salt thereof, a water swellable polymer, and a neutralizing agent, and b) a water insoluble film coating surrounding the tablet core, wherein the water insoluble film coated tablet core has a plurality of apertures. However, these formulations suffer from low bioavailability, high fluctuation in individual-to-individual variation and may result in unacceptable levels of bleeding in patients.

SUMMARY OF THE INVENTION

One embodiment of the present invention is a method of providing a therapeutic blood plasma concentration of DPOC-4088 over a 24 hour period, comprising orally administering to a patient in need thereof an extended release formulation comprising an effective amount of DPOC-4088 that provides a blood plasma concentration of DPOC-4088 of greater than 200 nM/100 mg administered over a period greater than 10 hours following a single oral dose.

The present invention also provides a method for providing thrombin inhibition over a 24 hour period comprising administering orally to a patient in need thereof an extended release formulation comprising an effective amount of DPOC-4088 that provides a ration of Cmax/C12 h of between about 2 and 3 and an AUC greater than about 8000 per 100 mg DPOC-4088 administered. In one aspect, the AUC is greater than about 8,500. In another aspect, the AUC is greater than about 9,000.

In another embodiment, there is provided a method of providing thrombin inhibition over a 24 hour period comprising administering orally to a patient in need thereof an extended release formulation comprising 199 mg of DPOC-4088 that has the following dissolution profile:

| Time (hours) | Average % DPOC-4088 Released |
|---|---|
| 1 | <10 |
| 2 | 5-15 |
| 4 | 20-35 |
| 6 | 35-50 |
| 8 | 50-65 |
| 10 | 65-75 |
| 12 | 75-90 |
| 14 | 85-100 |
| 16 | >95 |

The present invention also provides an extended release formulation of DPOC-4088 that is capable of maintaining substantially constant blood plasma levels of DPOC-4088 for at least about 16 hours, and which provides a degree of fluctuation of less than 8, after administration to a patient. In one aspect, the extended release formulation is capable of maintaining substantially constant blood plasma levels of DPOC-4088 for at least about 24 hours. In another aspect, the extended release formulation which provides a degree of fluctuation of less than 4.

There is also provided an extended release formulation of DPOC-4088 that (per 100 mg of DPOC-4088 in the formulation) is capable of achieving a steady state Cmax of less than or equal to 200 nM/mL, and a steady state Cmin of between about 150 and 250 nM/mL, wherein the ratio of Cmax to Cmin is less than about 8, after administration to a patient. In one aspect, the ratio of Cmax to Cmin is about 6. In another aspect, the ratio of Cmax to Cmin is about 2.

The present invention also provides a method of treating or preventing a thromboembolism, comprising administering the above extended release formulations to an individual in need thereof.

BRIEF DESCRIPTION OF THE DRAWINGS

FIG. 10a is a diagram showing mean aPTT Versus Time Curves After Administration of a Single Dose of 100 or 200 mg DPOC-4088 Formulated as a 16 hr Prolonged Release Formulation.

FIG. 10b is a diagram showing mean aPTT Versus Time Curves After Administration of a Single Dose of 100 or 200 mg DPOC-4088 Formulated as a 20 hr Prolonged Release Formulation.

FIG. 12a is a graph showing mean TT Versus Time Curves After Administration of a Single Dose of 100 or 200 mg DPOC-4088 Formulated as a 16 hr Prolonged Release Formulation.

FIG. 12b is a graph showing mean TT Versus Time Curves After Administration of a Single Dose of 100 or 200 mg DPOC-4088 Formulated as a 20 hr Prolonged Release Formulation.

DETAILED DESCRIPTION OF THE PREFERRED EMBODIMENTS

Figure 1:
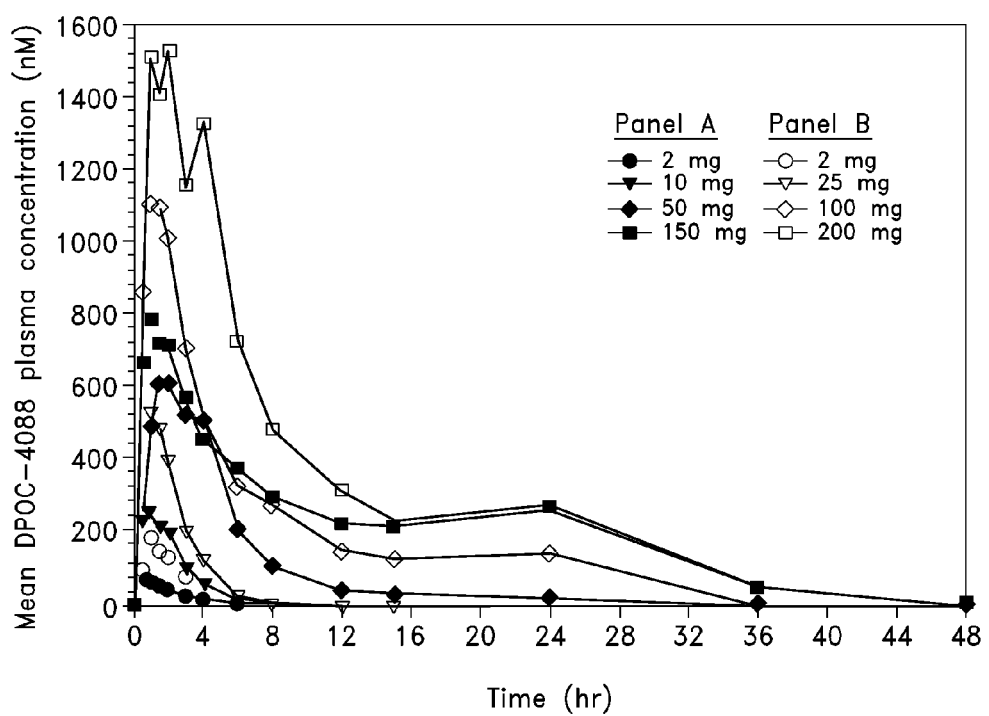
FIG. 1 is a graph showing mean DPOC-4088 plasma concentrations following single oral doses of an IR formulation in healthy young men.

In one embodiment, the present invention relates to administration of 3-fluoro-2-pyridylmethyl-3-(2,2-difluoro-2-(2-pyridyl)ethylamino)-6-chloropyrazin-2-one-1-acetamide (DPOC-4088), through an extended release formulation. This is based on the finding that through extending the release of active ingredient for over a period of time, substantial reduction in the degree of fluctuation of plasma levels of 3-fluoro-2-pyridylmethyl-3-(2,2-difluoro-2-(2-pyridyl)ethylamino)-6-chloropyrazin-2-one-1-acetamide is achieved resulting in constant plasma levels of the active ingredient and thereby reducing the frequency of dosing, eliminating the potential side effects that may be associated with immediate release formulation.

In one aspect, there is provided an extended release formulation of DPOC-4088 that after oral administration to a patient is capable of maintaining substantially constant plasma levels of the active ingredient for at least about 16 hours. In another aspect, the extended release formulation is capable of maintaining substantially constant plasma levels of the active ingredient for at least about 24 hours. In one embodiment, the extended release formulation may comprise 100 mg DPOC-4088. In other embodiments, the extended release formulation may comprise 50 mg, 150 mg, 200 mg, 300 mg, 400 mg, 500 mg, 600 mg, 700 mg, 800 mg, 900 mg, or 1,000 mg DPOC-4088.

In another embodiment, there is provided a method for providing a therapeutic blood plasma concentration of DPOC-4088 over a 24 hour period which comprises orally administering to a patient in need thereof an extended release formulation comprising 100 mg of DPOC-4088 that provides a blood plasma concentration of DPOC-4088 of greater than 200 nM/100 mg over a period greater than 10 hours, 12 hours, and preferably 16 hours following a single oral dose. In other embodiments, different amounts of DPOC-4088 are used, such as 50 mg, 150 mg, 200 mg, 300 mg, 400 mg, 500 mg, 600 mg, 700 mg, 800 mg, 900 mg, or 1,000 mg, which provide a blood plasma concentration of DPOC-4088 of greater than 200 nM per amount of DPOC-4088.

Another embodiment relates to a method for providing thrombin inhibition over a twenty four hour period which comprises administering orally to a patient in need thereof an extended release formulation comprising 100 mg of DPOC-4088 that provides a ratio of Cmax/C12 h of between about 2 and 3 and/or a ratio of Cmax/C24 h of between about 2 and about 5 and/or an area under the curve (AUC) greater than about 7500 per 100 mg administered, or greater than about 8000 per 100 mg administered, or greater than about 8500 per 100 mg administered, or preferably greater than about 9000 per 100 mg administered. In other embodiments, different amounts of DPOC-4088 are used, such as 50 mg, 75 mg, 125 mg, 150 mg, 200 mg, 300 mg, 400 mg, 500 mg, 600 mg, 700 mg, 800 mg, 900 mg, or 1,000 mg, which provide the above-referenced values.

In another embodiment, there is provided a method of providing thrombin inhibition over a twenty four hour period which comprises administering orally to a patient in need thereof an extended release formulation comprising DPOC-4088 that has the following dissolution profiles

TABLE 1

| Time (h) | Average % DPOC-4088 Released | | |
|---|---|---|---|
| 2 h | NMT 20 | NMT 20 | NMT 20 |
| 6 h | 20 to 50 | 30 to 50 | 20 to 45 |
| 12 h | 50 to 90 | 70 to 90 | 50 to 80 |
| 16 h | NLT 65 | NLT 85 | NLT 70 |
| 24 h | NLT 85 | NLT 90 | NLT 85 |

In another embodiment, there is provided a method of providing thrombin inhibition over a twenty four hour period which comprises administering orally to a patient in need thereof an extended release formulation comprising 100 to 200 mg of DPOC-4088 that has the following dissolution profile:

TABLE 2

| Time (h) | Average % DPOC-4088 Released |
|---|---|
| 1 | <20 |
| 2 | 5-15 |
| 4 | 20-35 |
| 6 | 35-50 |
| 8 | 50-65 |
| 10 | 65-75 |
| 12 | 75-90 |
| 14 | 85-100 |
| 16 | >95 |

In another aspect, the extended release formulation exhibits an in vitro release of the active ingredient such that at least about 90% of the active ingredient is released after 16 hours. The formulation further provides substantially constant release of the active ingredient until about 90% of the active ingredient is released from the dosage form.

In another embodiment, the extended release formulation after oral administration to a patient provides a degree of fluctuation of less than 8 in plasma levels of the active ingredient. Preferably the extended release formulation provides a degree of fluctuation of less than 4.

In one embodiment, the extended release formulations are capable of achieving a steady state maximal plasma concentration (Cmax) of less than or equal to about 2000 nM/mL and preferably less than or equal to about 1600 nM/mL and a steady state minimal plasma concentration (Cmin) between about 150 and about 250 nM/mL and preferably about 200 nM/mL. Preferred ratios of maximum plasma concentration at steady-state to minimum plasma concentration at steady-state (Cmax,ss/Cmin,ss) are less than about 8, with the range of about 6 to about 2 being more preferred. Further preferred is a Cmax,ss/Cmin,ss ratio of about 4. These values are per 100 mg of DPOC-4088 in the formulation.

In another embodiment, the extended release formulations are capable of providing an increase of about 1.5 to about 2.5 fold over baseline in the ecarin clotting time (ECT) at the steady-state trough plasma concentration (Cmin,ss), and preferably an increase of about 2 fold over baseline in the ecarin clotting time (ECT).

In still another embodiment, the extended release formulations are capable of providing at least about a 2-fold increase in ECT and/or at least about a 1.5-fold increase in aPTT at trough steady-state levels.

Further embodiments relate to use of the extended release formulation for treating or preventing thromboembolism.

The term "extended release" in respect to the formulations disclosed herein means that the formulation does not immediately release the active ingredient to the environment (e.g., blood, stomach, intestine, colon), but rather releases the active ingredient over a predetermined amount of time. Thus, relatively constant or predictably varying amounts of the active agent can be delivered over a specified period of time. Expressions such as "prolonged action," "repeat-action," "sustained release", "modified release" and "controlled release" have also been used to describe such formulations or dosage forms. An extended release can therefore be described as a dosage form or a formulation that allows at least a two-fold reduction in dosing frequency as compared to a conventional immediate release dosage form.

As used herein, the term "active ingredient" means 3-fluoro-2-pyridylmethyl-3-(2,2-difluoro-2-(2-pyridyl)ethylamino)-6-chloropyrazin-2-one-1-acetamide (DPOC-4088), pharmaceutically acceptable salts thereof, and derivatives that produce similar localized or systemic effect or effects in animals. Derivatives of the active ingredient, such as esters, ethers and amides without regard to their ionization and solubility characteristics can be used alone or mixed with other compounds. Also, prodrugs of the active agent can be used in a form that, upon release from the tablet, is converted by enzymes, hydrolyzed by body pH or converted by other metabolic processes, to the original form, or to a biologically active form. That is, prodrugs are specifically included within the definition of pharmaceutically active ingredients. In addition, racemic mixtures and separated enantiomers of the active ingredient are also contemplated. Furthermore, hydrates as well as anhydrous compositions and polymorphs of the active ingredient are included in the compositions described herein.

As used herein, the term "pharmaceutically acceptable salts" means non-toxic salts of the active ingredients which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

As used herein. the term "substantially constant" with respect to the plasma levels of active ingredient means that the plasma profile after oral administration of the extended release formulation does essentially not exhibit any substantial peaks. This may also be illustrated numerically such that a constant plasma level of at least about 200 nM is maintained for at least about 16 hours after administration. This is further demonstrated by reduced degree of fluctuation.

As used herein, the term "Degree of Fluctuation (DFL)" refers to a numerical expression $C_{max}/C_{24}$ which is less than 8, preferably less than 4 as provided by administration of the extended release formulations described herein.

As used herein, the term "substantially constant" in relation to the in vitro release of the active ingredient from the extended release formulation means the release rate at any time point till 90% of the active ingredient is released from the formulation, should not deviate by not more than 50% of the mean release rate of the active ingredient.

As used herein, the term "activated partial thromboplastin time (aPTT)" is the period required for clot formation in recalcified blood plasma after contact activation and the addition of platelet substitutes. This measure is used to address the intrinsic and common pathways of coagulation.

As used herein, the term "ecarin clotting time (ECT)" is used to monitor anticoagulation during treatment with hirudin, an anticoagulant which was originally isolated from leech saliva. Ecarin, the primary reagent in the assay, is derived from the venom of the saw-scaled viper, *Echis carinatus*. In the assay, a known quantity of ecarin is added to the plasma of a patient treated with hirudin. Ecarin activates prothrombin through a specific proteolytic cleavage, which produces meizothrombin, a prothrombin-thrombin intermediate which retains the full molecular weight of prothrombin, but possesses a low level of procoagulant enzymatic activity. This activity is inhibited by hirudin and other direct thrombin inhibitors, but not by heparin. ECT is prolonged in a specific and linear fashion with increasing concentrations of hirudin.

As used herein, the term "thrombin time (TT)" is the time required for plasma fibrinogen to form thrombin, measured as the time for clot formation after exogenous thrombin is added to citrated plasma.

As used herein, the term "prothrombin time (PT)" is the rate at which prothrombin is converted to thrombin in citrated blood with added calcium. This is used to assess the extrinsic coagulation system of the blood Although any conventional method well known in the art may be used to measure in vitro drug release, release of DPOC-4088 in the present examples in vitro drug release was measured using a test that utilizes United States Pharmacopeia dissolution apparatus II (with stationary basket) rotated at 50 rpm with 900 ml of 0.1 N HCl at 37° C.

The present formulations are not restricted to any particular type of formulation. Thus, various types of extended or controlled release formulations may be used, such as, for example, osmotic tablets, tablets coated with sustained release polymers, coated or uncoated gel matrix tablets, coated beads, pellet formulations, multi-layer formulations, capsules, gelcaps and the like.

An exemplary extended release formulation comprises a tablet core comprising the active ingredient, a matrix forming polymer that modulate the release of the active ingredient from the core, optionally a surfactant and other conventional pharmaceutical excipients known in art. The tablet may further be coated with a functional or non-functional coating.

As an active ingredient, DPOC-4088 may be present in any amount suitable for the desired treatment of a patient. Generally the amount of DPOC-4088 in the extended release formulations ranges from about 25 mg to 400 mg. In other embodiments, the amount of DPOC-4088 ranges from about 50 mg to 250 mg, or from about 100 mg to 200 mg.

In one embodiment, the matrix forming polymers constituting the matrix are mainly responsible for modulating the release profile of the preparation. Depending on the amount of polymers processed in the preparation, the release profile can be adjusted. In general, the amount of matrix forming polymer in the present formulation ranges from about 0.01 to about 80% (w/w). In other embodiments, the amount of matrix forming polymer ranges from about 1% to about 60% by weight of the formulation, or from about 10% to about 50% by weight of the formulation.

The matrix forming polymer may be any polymer which is either hydrophilic or hydrophobic in nature. Suitable hydrophilic polymers include, but are not limited to, alkylcelluloses such as methyl cellulose, hydroxyalkyl celluloses such as hydroxymethyl cellulose, hydroxyethyl cellulose, hydroxypropyl cellulose and hydroxybutyl cellulose, hydroxyalkyl alkyl celluloses such as hydroxyethyl methyl cellulose and hydroxypropyl methyl cellulose, carboxyalkyl celluloses such as carboxymethyl cellulose, alkali metal salts of carboxyalkyl celluloses such as sodium carboxymethyl cellulose, carboxyalkylalkyl celluloses such as carboxymethylethyl cellulose, carboxyalkyl cellulose esters, starches, pectines such as sodium carboxymethyl amylopectine, chitin derivates such as chitosan, disaccharides, oligosaccharides and polysaccharides such as trehalose, alginic acid, alkali metal and ammonium salts thereof, carrageenans, galactomannans, tragacanth, agar-agar, gum arabicum, guar gum and xanthan gum, polyacrylic acids and the salts thereof, polymethacrylic acids, the salts and esters thereof, methacrylate copolymers, polyvinylalcohol, polyvinylpyrrolidone, polyvinylpyrrolidone-vinylacetate copolymers, combinations of polyvinylpyrrolidone and polyvinylalcohol, polyalkylene oxides such as polyethylene oxide and polypropylene oxide and copolymers of ethylene oxide and propylene oxide. Two or more of these polymers also can be used in any desired combination.

Suitable hydrophobic matrix forming polymers include, but are not limited to, ethyl cellulose, chitin, chitosan, cellulose esters, aminoalkyl methacrylate polymer, anionic polymers of methacrylic acid and methacrylates, copolymers of acrylate and methacrylates with quaternary ammonium groups, ethylacrylate methylmethacrylate copolymers with a neutral ester group, polymethacrylates, surfactants, aliphatic polyesters, zein, polyvinyl acetate, polyvinyl chloride, and the like.

Hydrophilic polymers suitable for use in the compositions described herein include polysaccharides such as cellulose derivatives and cellulose ether derivatives. Hydrophobic polymers include ethylcellulose, cellulose acetate, polymethacrylates and aminoalkyl methacrylate copolymers. Cellulose ether derivatives include hydroxypropyl methylcellulose and hydroxypropyl cellulose.

Since DPOC-4088 is a poorly soluble drug, extended release formulations of DPOC-4088 with improved dissolution characteristics of DPOC-4088 may be achieved through use of a surfactant. In general, the ratio of the surfactant to the active ingredient is between 0.01 and 1.

Exemplary surfactants include, but are not limited to, anionic surfactants such as sodium lauryl sulphate, sodium docusate, polyoxyethylene alkyl ethers (macrogols), cationic surfactants like quaternary ammonium (cetrimide), cetylpyridinium chloride, cetyltrimethyl ammonium bromide, and pyridinium cationic surfactants; non-ionic surfactants such as Sorbitan esters (e.g., span 40, 60, 80), polyoxyethylene sorbitan fatty acid esters (e.g., polysorbate 20, 40, 60, 80), polyoxyethylene stearates, Polyoxylglycerides, poloxamers (e.g., pluronic F68, pluronic F127), glycerylmono oleate, polyoxyethylenesorbitan monolaurate (e.g., Tween), polyethylene glycol tert-octylphenyl ether (e.g., Triton) combinations thereof and other similar materials known to one of ordinary skill in the art.

Conventional pharmaceutical excipients are materials that are considered safe and effective and may be administered to an individual without causing undesirable biological side effects or unwanted interactions. Conventional excipients include, but are not limited to diluents, binders, disintegrating agents, lubricants, pH modifying agents, anti-adherents, fillers, pigments, colorants, stabilizing agents, flavoring agents, glidants and combinations thereof. In general, the amount of excipient ranges between about 10% and about 70%.

Suitable fillers include, but are not limited to, lactose such as lactose monohydrate, lactose anhydrous and Pharmatose DCL21 including anhydrous, monohydrate and spray dried forms; sucrose; microcrystalline celluloses such as Avicel PH 101, Avicel PH 102, Avicel PH 112, Avicel PH 200, Avicel PH 301 and Avicel PH 302; trehalose; maltose; mannitol; sorbitol; inulin; dibasic calcium phosphate; tricalcium phosphate; saccharides like soy polysaccharides, calcium sulfate, or any other inert filler known to one of ordinary skill in the art. In general, the weight percentage of filler ranges between about 1% and about 90% (w/w).

Suitable binders include, but are not limited to, starch, povidone, hydroxypropyl methyl cellulose, pregelatinised starch, hydroxypropyl cellulose and/or mixtures of the foregoing. Suitable lubricants, including agents that act on the flowability of the powder to be compressed are, for example, colloidal silicon dioxide such as Aerosil 200, talc, stearic acid, magnesium stearate, calcium stearate and sodium stearyl fumarate and combinations and mixtures thereof. In general, the weight percentage of the binder ranges between about 0.1% and about 20% (w/w).

Suitable disintegrants include, for example, lightly cross-linked polyvinyl pyrrolidone, corn starch, potato starch, maize starch and modified starches, croscarmellose sodium, cross-povidone, sodium starch glycolate and combinations and mixtures thereof. In general, the weight percentage of disintegrants ranges between about 0.1% and about 10% (w/w).

Other excipients and adjuvants include lubricants such as stearic acid, magnesium stearate, calcium stearate sodium stearyl fumarate, glycerol tribehenate, etc.; flow control agents such as colloidal silica, light anhydrous silicic acid, crystalline cellulose, talc, etc.; crystallization retarders such as povidone etc.; coloring agents, including dyes and pigments such as iron oxide Red or Yellow, titanium dioxide, talc, etc; and mixtures of two or more of these excipients and/or adjuvants.

The formulations described herein can be prepared using techniques well known in the art. The tablet core can be prepared by wet granulation process. Alternatively, the tablet core can be prepared using dry granulation or direct compression. In one embodiment, the tablet core comprises an amount of DPOC-4088 of between about 10% and about 50% by weight of the total core mass.

The tablet core may further be coated with one or more modified release coatings, which further modulate the release of the active agent from the core or central layer. Suitable coatings include taste mask coatings, enteric coatings, sustained or extended release coatings, and delayed release coatings. The dosage forms may also be coated for aesthetic reasons such as to impart a color to the dosage form or to apply a surface finish to the dosage form.

The tablet core can be coated with a film coat using techniques well known in the art. The coatings can be applied as a solid or as an aqueous suspension or organic solution. Suitable techniques for applying the coating include, but are not limited to, spray coating, pan coating, fluid bed coating, and compression coating. The coating may be applied to a thickness of from about 10 to about 1,000 µm, e.g. 100, 250, 500 or 750 µm. In a preferred embodiment, the film thickness is between about 100 and 500 µm. In one embodiment, the coating is formed over the entire surface of the core.

Examples of suitable coating materials include, but are not limited to, cellulose polymers, such as hydroxypropyl cellulose, hydroxypropyl methylcellulose, ethyl cellulose, cellulose acetate phthalate, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Rohm Pharma). Additionally, the coating material may contain conventional carriers such as plasticizers, pigments, colorants, glidants, stabilization agents, and surfactants.

The formulations described herein can be administered in general to treat thromboembolic disorders and in particular for the treatment and/or prevention of venous and cardiogenic thromboembolism. For example, the formulations can be used in the prevention of venous thromboembolic events in patients following surgery, such as hip or knee replacement, or they can be used for risk reduction of stroke and systemic embolism in patients with atrial fibrillation, including non-valvular atrial fibrillation. The formulations are generally administered orally preferably in the form of a tablet. The composition can be administered in a single dose, an escalating dose, or administered at an elevated dosage which is then decreased to a lower dosage after a particular circulating blood concentration of the compound has been achieved.

The tables below provide dissolution profiles of useful extended release formulations that can be used to practice the invention. Extended release formulations have the following dissolution profiles have beneficial pharmacokinetic and therapeutic properties.

TABLE 3

Acceptable Dissolution Rates

| Time (h) | Average % DPOC-4088 Released |
|---|---|
| 2 | <15 |
| 4 | 15-30 |
| 6 | 20-50 |
| 8 | 30-60 |
| 12 | 55-85 |
| 14 | 65-95 |
| 16 | 75-100 |
| 20 | >95 |

TABLE 4

Preferred Dissolution Rate

| Time (h) | Average % DPOC-4088 Released |
|---|---|
| 1 | <5 |
| 2 | 5-10 |
| 4 | 15-20 |
| 6 | 25-35 |

TABLE 4-continued

Preferred Dissolution Rate

| Time (h) | Average % DPOC-4088 Released |
|---|---|
| 8 | 35-45 |
| 10 | 45-55 |
| 12 | 55-65 |
| 14 | 65-75 |
| 16 | 70-85 |
| 20 | 85-100 |
| 24 | >95 |

TABLE 5

Further Preferred Dissolution Rates

| Time (h) | Average % DPOC-4088 Released |
|---|---|
| 1 | <10 |
| 2 | 5-15 |
| 4 | 20-35 |
| 6 | 35-50 |
| 8 | 50-65 |
| 10 | 65-75 |
| 12 | 75-90 |
| 14 | 85-100 |
| 16 | >95 |

EXAMPLES

Reference Example 1

Immediate Release (IR) Formulation of DPOC-4088

A single oral rising-dose study in 34 healthy subjects (24 males, 10 females) evaluated the safety, tolerability, plasma concentration-time profile and pharmacodynamics of an IR-formulation of DPOC-4088. The study was double-blinded, randomized, and placebo-controlled. The safety conclusions were that single oral doses of the IR formulation from 2 to 200 mg in healthy males and doses of 100 mg in healthy females were well-tolerated.

The mean PK parameters of DPOC-4088 IR formulation following single oral doses in healthy male volunteers are shown in Table 6. Mean peak and 12 hour plasma concentration of ~1330 nM and ~150 nM, respectively, were achieved at the 100-mg dose. For the 200 mg dose, the mean peak and 12 hour plasma concentrations were 2344 nM and 316 nM, respectively.

TABLE 6

Summary of PK data for single oral doses of the IR formulation of DPOC-4088 in healthy males

| Dose mg | AUC0-∞ μM · hr | Cmax nM | Tmax Hr | $t_{½}^{a}$ Hr | C12 hr nM |
|---|---|---|---|---|---|
| 2 | 0.18 (0.05) | 89.1 (28.0) | 0.75 (0.42) | 1.06 | — |
|  | [0.11 to 0.25] | [55 to 128] | [0.5 to 1.5] | [1.00 to 1.23] |  |
| 5 | 0.5 (0.3) | 204 (82.2) | 1.1 (0.5) | 1.1 | 1.2 (2.6) |
|  | [0.16 to 1.07] | [93 to 340] | [0.5 to 2.0] | [0.8 to 1.93] | [0.3 to 6.5] |
| 10 | 0.7 (0.2) | 362 (123) | 0.92 (0.58) | 1.1 | 0.4 (0.3) |
|  | [0.52 to 0.97] | [202 to 551] | [0.5 to 2.0] | [0.94 to 1.16] | [0.3 to 0.9] |
| 25 | 1.3 (0.4) | 599 (164) | 1.2 (0.5) | 4.0 | 1.9 (2.0) |
|  | [0.79 to 1.95] | [424 to 775] | [0.5 to 2.0] | [1.2 to 8.6] | [0.3 to 5.8] |
| 50 | 3.5 (0.75) | 868 (215) | 2.3 (1.1) | 4.1 | 38.8 (22.7) |
|  | [2.4 to 4.7] | [556 to 1199] | [1 to 4] | [3.6 to 5.0] | [14.4 to 72.4] |
| 100 | 7.6 (3.2) | 1330 (351) | 1.0 (0.6) | 3.0 | 148 (107) |
|  | [4.7 to 12.1] | [1004 to 1995] | [0.5 to 2.0] | [2.5 to 3.6] | [53 to 332] |
| 150 | 9.8 (0.9) | 873 (294) | 1.2 (1.0) | 4.9 | 223 (78) |
|  | [8.8 to 11.1] | [500 to 1209] | [0.5 to 3.0] | [3.8 to 5.9] | [155 to 329] |
| 200 | 14.1 (10.3) | 2342 (1869) | 1.8 (1.2) | 3.2 | 316 (235) |
|  | [6.3 to 32.7] | [501 to 5781] | [1 to 4] | [2.4 to 5.0] | [125 to 717] |

Data are means (SD) [range];
[a] Harmonic mean.

As is displayed in FIG. 1, plasma levels peaked early and declined rapidly at low doses (≤25 mg) with an apparent half-life of 1 to 2 hours. At doses of 50 mg and above, there were early peaks in plasma concentration but also a slower decline suggesting prolonged absorption of DPOC-4088 along the GI tract. AUC and $C_{max}$ increased less than proportionally with doses of 100 mg and higher. Estimates of within-subject variance (CV) were 24.2% (95% CI, 18.8, 33.9) for the AUC and 37.7% (95% CI, 29.3, 53.6) for $C_{max}$.

Exposure to DPOC-4088 using the IR formulation was comparable under both fasted and fed conditions. Food delayed the time to peak plasma concentration with a mean time to reach the maximal plasma concentration ($T_{max}$) under fasted vs fed conditions of 1.1 and 2.4 hours, respectively.

Reference Example 2

Comparison of 50 Mg DPOC-4088 at Different Release Rates of the Drilled Formulations Described in US 2004/0213850

Ten subjects (fasting) received each of 5 treatments in a randomized crossover design: 50 mg of DPOC-4088 at 3 release rates of the drilled formulation, 50 mg of the IR formulation, or placebo. The average dose delivered by the 31-hole, 18-hole, and 10-hole tablets was 41.1, 36.6, and 36.4 mg, respectively, or 82, 73, and 73% of the drug load.

The drilled formulations provided a delayed and decreased peak concentration and a decreased peak-to-trough ratio compared to IR. In addition, the slower the release rate, the greater the reduction in $C_{max}$ and peak-to-trough ratio (Table). The geometric mean ratio of $C_{max}$ to $C_{12hr}$ was 5.0, 2.8, and 2.4 for the 31-hole, 18-hole, and 10-hole formulations, respectively, compared to 22 for the IR capsule. Following administration of the 10-hole formulation, all subjects had $C_{max}/C_{12}<4$. $C_{max}$ and AUC data (Table) indicate a reduced peak concentration with accompanying reduction in AUC compared to the IR formulation. The bioavailability of the 31-hole, 18-hole, and 10-hole tablets was 63, 51, and 44%, respectively, relative to IR (Table 7).

TABLE 7

Observed mean PK parameters of DPOC-4088 following single doses of 50 mg 31-hole, 18-hole, or 10-hole tablets or 50-mg IR capsule.

| Parameter ± SD | 31-hole Tablet N = 10 | 18-hole Tablet N = 11[a] | 10-hole Tablet N = 11[a] | IR N = 10 |
|---|---|---|---|---|
| Cmax (nM) | 310.5 (139.4) | 225.0 (119.4) | 151.7 (70.0) | 1016 (327.7) |
| Tmax (hr) | 4.0 (3.0) | 4.4 (2.0) | 4.3 (1.8) | 1.4 (0.9) |
| AUC48 (nM · hr) | 2877 (1255) | 2778 (1862) | 2263 (1252) | 4473 (1747) |
| Geometric mean Cmax/C12 [Range] | 5.0 [1.0-17.2] | 2.8 [1.7-9.7] | 2.4 [1.2-3.9] | 22 [5.5-112] |
| Observed relative bioavailability[b] | 0.63 | 0.51[c] | 0.44[c] | — |

[a]Means include one subject who discontinued after completing the 18-hole and 10-hole tablet treatments.
[b]Geometric Mean AUC48 Ratio (drilled/IR), calculated using observed drilled AUC values.
[c]N = 10 one subject discontinued prior to completing IR treatment.

The IR formulation exhibited a short $t_{1/2}$, peak-to-trough ratios above 8, and a potential for within-subject variability.

Reference Example 3

Figure 2:
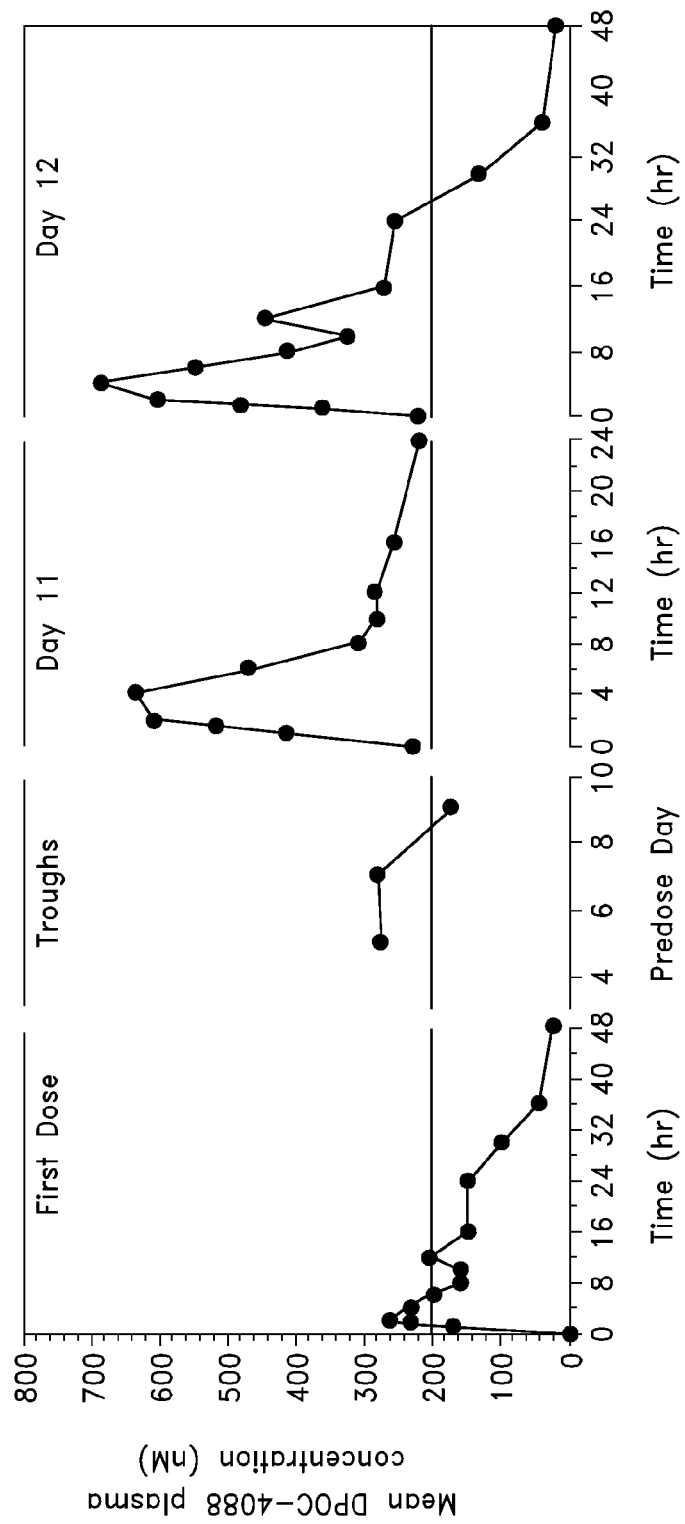
FIG. 2 is a graph showing plasma-concentration of DPOC-4088 100 mg 16-hr GEM formulation after single and multiple-dose administration.

Plasma-Concentration of DPOC-4088 100 Mg 10 Holes Per Face Formulation of US 2004/0213850 after Single- and Multiple-Dose Administration A randomized, double-blind, placebo-controlled, study that investigated the safety, tolerability, plasma concentration-time profile, and thrombin inhibitory activity of multiple oral doses of DPOC-4088 10-hole tablet formulation given Q24 hours for 11 days. A total of 10 subjects received 100 mg oral DPOC-4088 10-hole tablet (n=8) or placebo (n=2) in the morning (~9 AM) of Day 1 followed by 100 mg Q24 hour (~9 AM) in the morning of Days 3 to 12. Subjects were sequestered during the PK sampling periods only (Days 1 to 3 and Days 11 to 14) and returned to the clinical research unit each morning for dosing on Days 4 to 10. Plasma samples were collected for 48 hours following study drug administration on Days 1 and 12, and for the 24 hours following study drug administration on Day 11 for DPOC-4088 plasma concentrations. Plasma samples were also collected predose on Days 5, 7, and 9 for trough DPOC-4088 plasma concentrations. For the PD assessment, coagulation tests (aPTT, ECT, TT, PT and plasma fibrinogen) were collected on Days 1 to 3, 5, 7, 9, and Days 11 to 14. FIG. 2 shows the mean (n=8) plasma concentration profiles of DPOC-4088 following single and multiple dose administration of 100 mg 10-hole formulation. The blue reference line at 200 nM is the concentration anticipated for anticoagulant efficacy.

Figure 3:
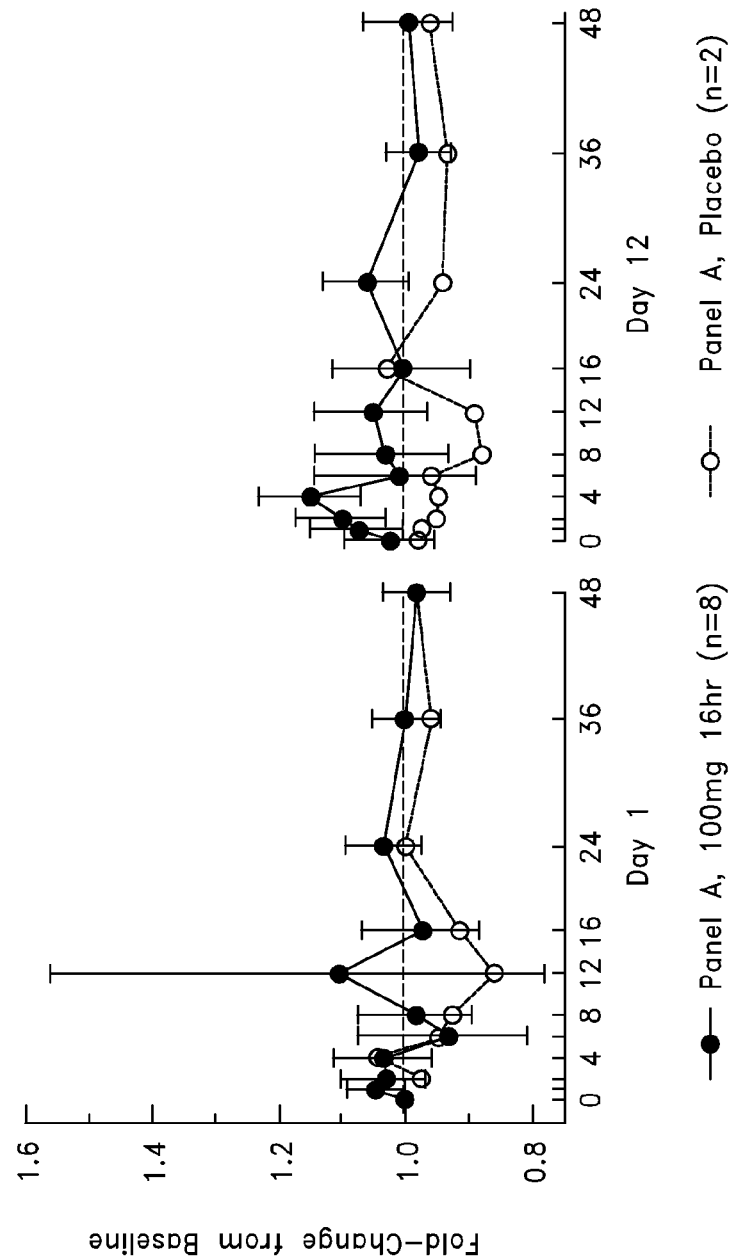
FIG. 3 is a graph showing geometric-mean fold change in aPTT from baseline following multiple oral 100 mg doses of the 10-hole formulated DPOC-4088.
Figure 4:
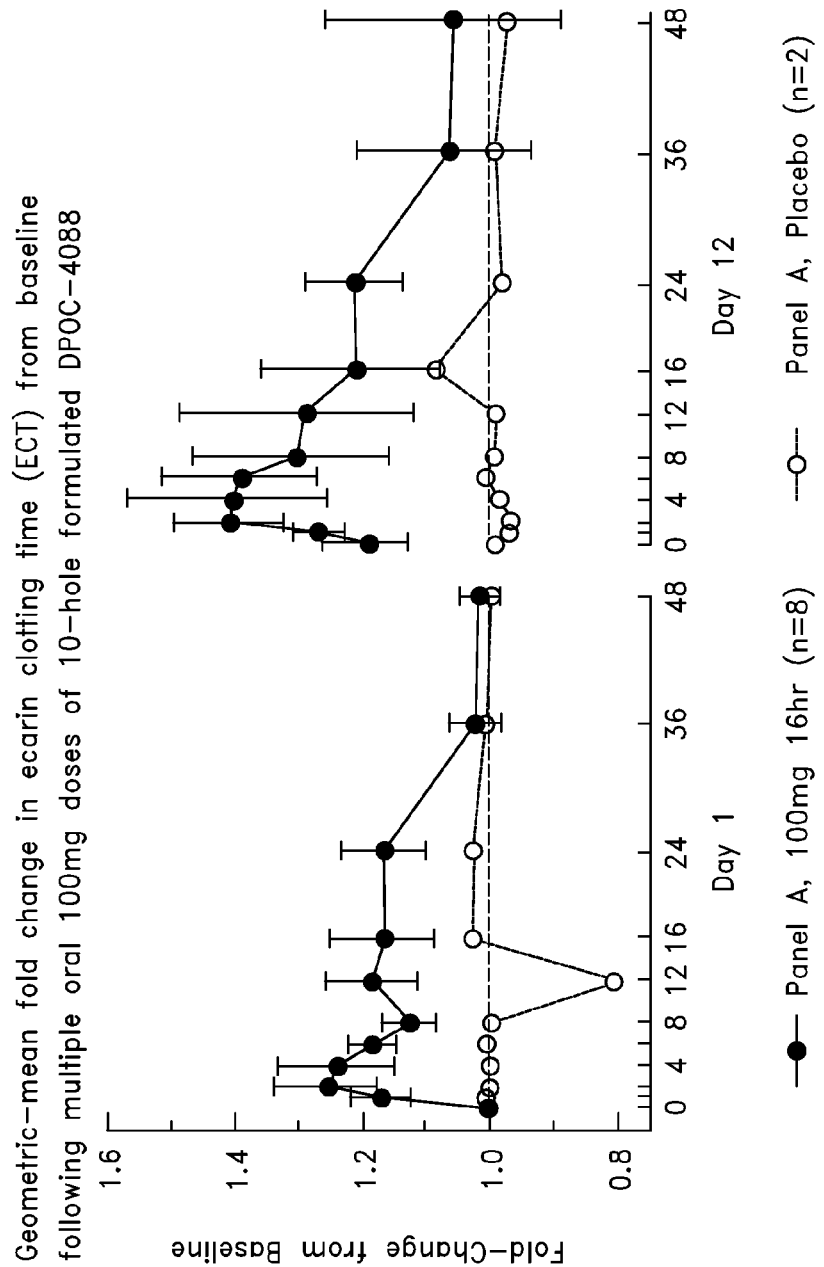
FIG. 4 is a graph showing geometric-mean fold change in ecarin clotting time (ECT) from baseline following multiple oral 100 mg doses of 10-hole formulated DPOC-4088.
Figure 5:
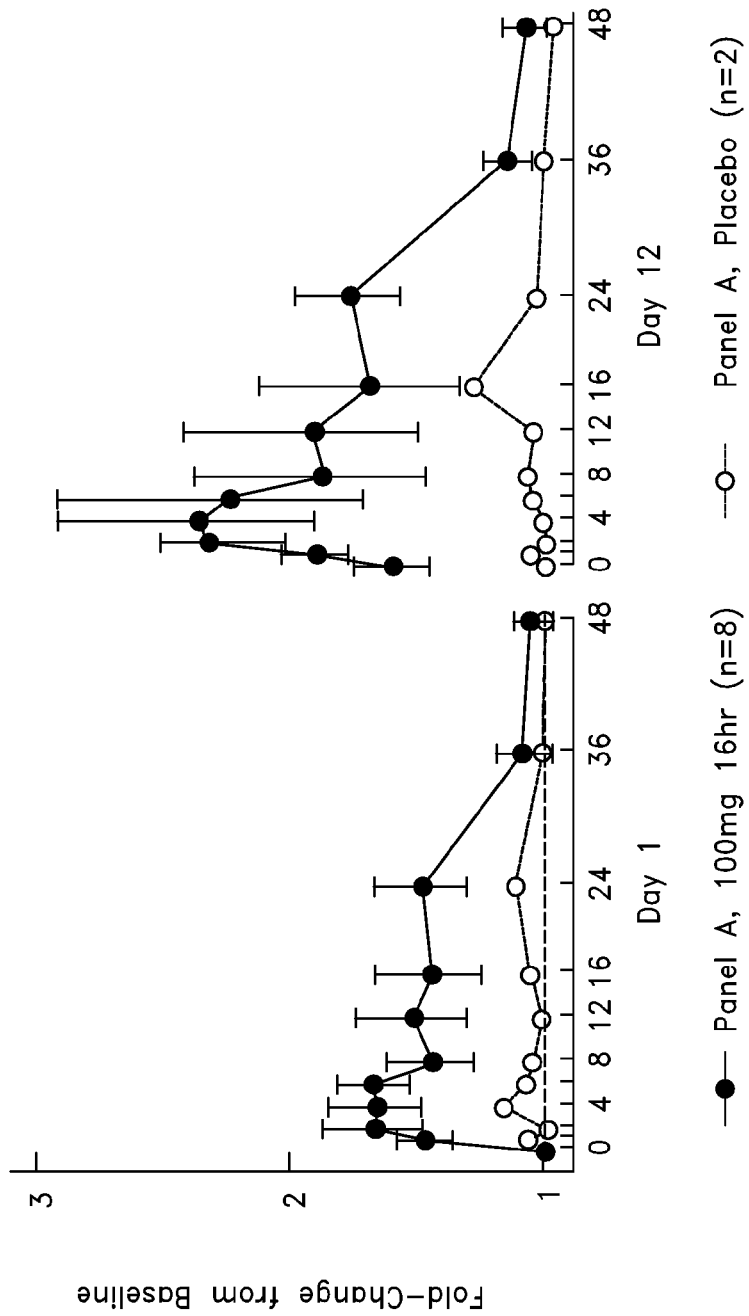
FIG. 5 is a graph showing geometric-mean fold change in thrombin time (TT) from baseline following multiple oral 100 mg doses of 10-hole formulated DPOC-4088
Figure 6:
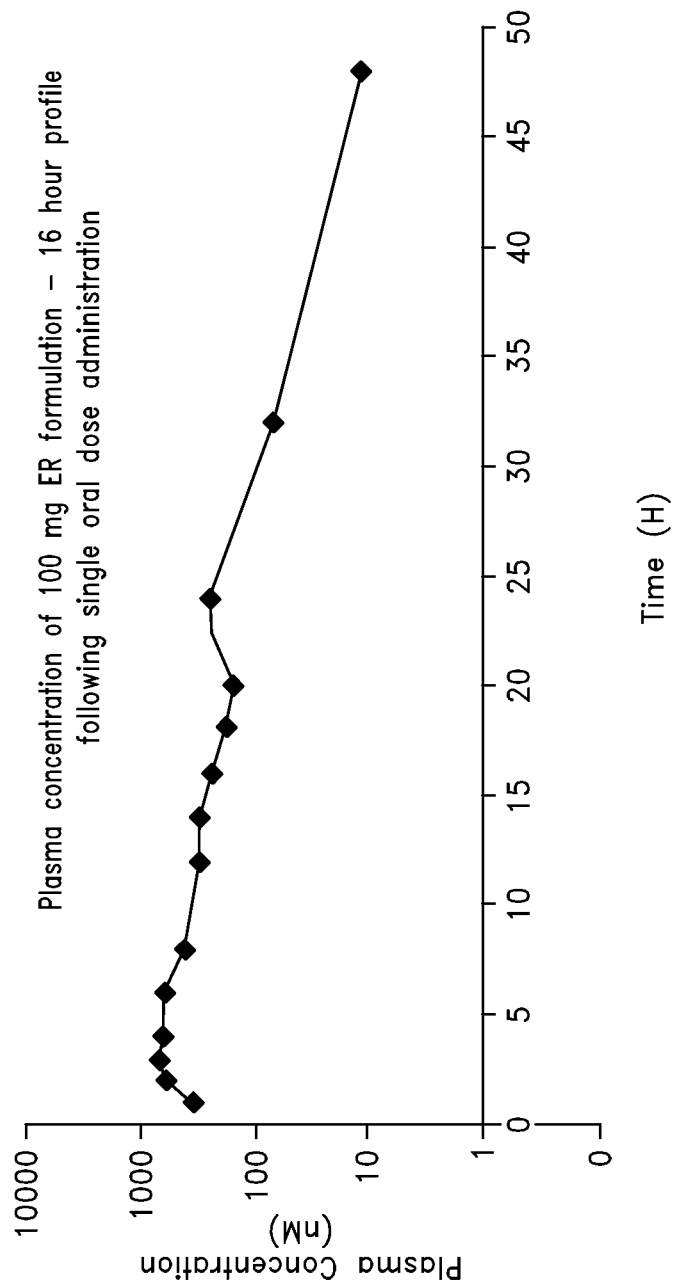
FIG. 6 is a diagram showing variation of Plasma concentration of DPOC-4088 (nM/ml) with time (hours) during 48 hours, when administering an 16 hour extended release formulation containing 100 mg of DPOC-4088.
Figure 7:
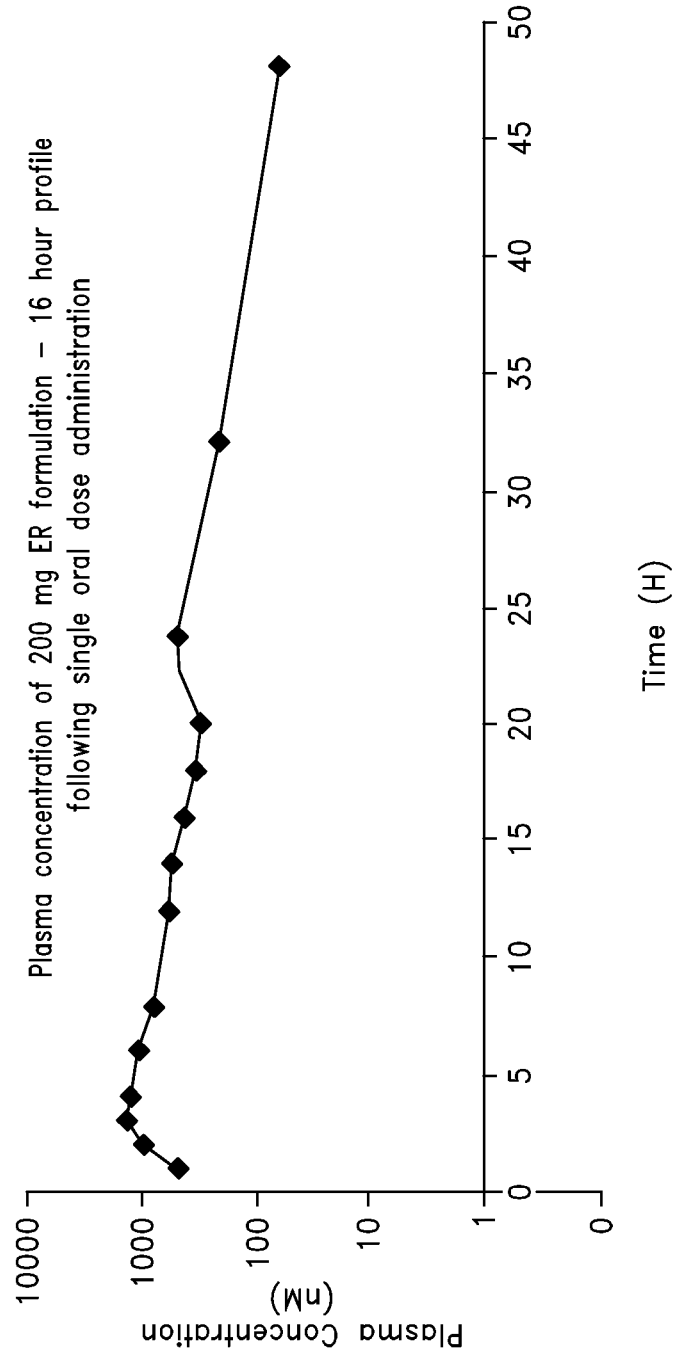
FIG. 7 is a diagram showing variation of Plasma concentration of DPOC-4088 (nM/ml) with time (hours) during 48 hours, when administering an 16 hour extended release formulation containing 200 mg of DPOC-4088.
Figure 8:
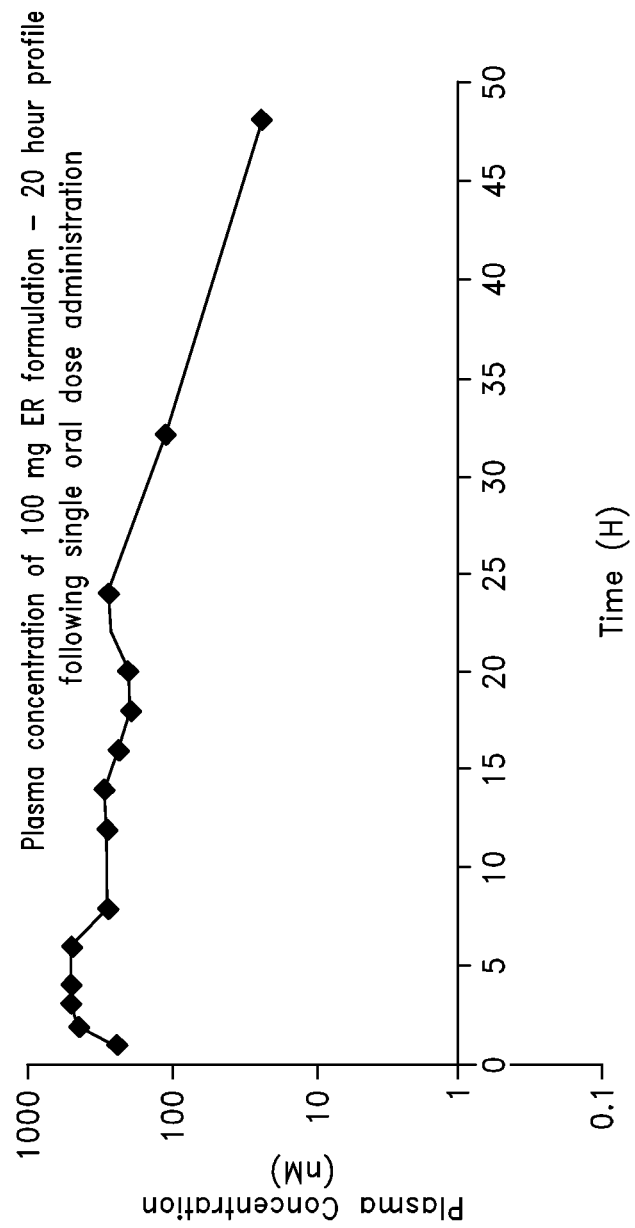
FIG. 8 is a diagram showing variation of Plasma concentration of DPOC-4088 (nM/ml) with time (hours) during 48 hours, when administering an 20 hour extended release formulation containing 100 mg of DPOC-4088.
Figure 9:
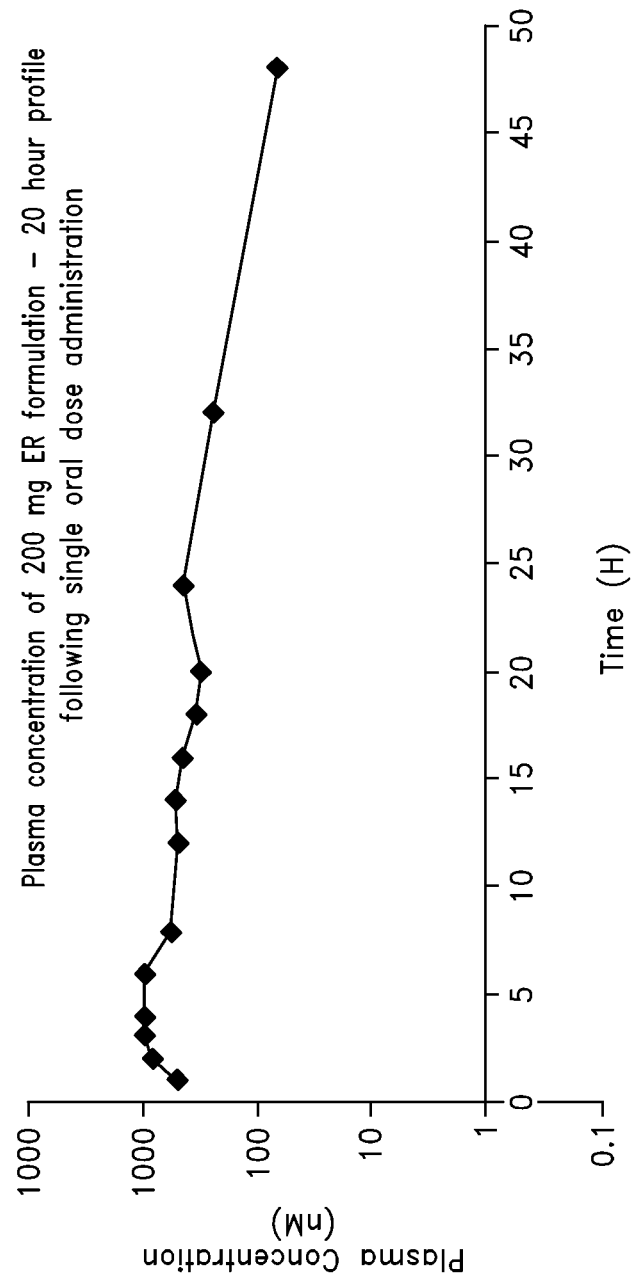
FIG. 9 is a diagram showing variation of Plasma concentration of DPOC-4088 (nM/ml) with time (hours) during 48 hours, when administering an 16 hour extended release formulation containing 200 mg of DPOC-4088.

Following multiple doses of 100 mg DPOC-4088 in the 10-hole tablet formulation given for a total of 11 days (first dose on Day 1, doses 2-10 on Days 3-12), the aPTT response was lower than expected, as shown in FIG. 3. The ECT and TT responses were more apparent, as shown in FIGS. 4 and 5.

Example 1

Four Formulations Formulation A, Formulation B, Formulation C And Formulation D were prepared. These formulations are described in Table 8.

TABLE 8

| S. No | Component TABLET CORE | Qty/Unit (mg)* Formulation A | Formulation B | Formulation C | Formulation D |
|---|---|---|---|---|---|
| 1 | DPOC-4088 | 100.00 | 200.00 | 100.00 | 200.00 |
| 2 | Mannitol Ph. Eur. (Pearlitol 25C) | 27.375 | 69.75 | 17.50 | 54.75 |
| 3 | Povidone Ph. Eur. (Plasdone-K29/32) | 15.00 | 30.00 | 15.00 | 30.00 |
| 4 | Poloxamers Ph. Eur. (Lutrol Micro 127) | 25.00 | 50.00 | 25.00 | 50.00 |
| 5 | Hypromellose Ph. Eur. (Methocel K4 MCR) | 60.00 | 75.00 | 90.00 | 120.00 |
| 6 | Silica Colloidal Anhydrous Ph. Eur. (Aerosil 200) | 2.50 | 5.00 | 2.50 | 5.00 |
| 7 | Ferric Oxide NF (Red Oxide of Iron) (E172) | 0.25 | 0.50 | 0.50 | 0.50 |

TABLE 8-continued

| S. No | Component TABLET CORE | Qty/Unit (mg)* | | | |
|---|---|---|---|---|---|
| | | Formulation A | Formulation B | Formulation C | Formulation D |
| 8 | Magnesium stearate Ph. Eur. | 2.375 | 4.75 | 2.50 | 4.75 |
| | Total | 232.50 | 435.00 | 253.00 | 465.00 |

The formulations described above are prepared as follows, and the preparation is summarized in the flow chart below. It should be noted that these components and steps are only one embodiment of the formulations described herein, and may be modified in accordance with well known pharmaceutical methods.

1. Mannitol and Ferric Oxide are passed through Quadro Comil.
2. DPOC-4088, Poloxamer, Silica Colloidal Anhydrous and Hypromellose are passed along with materials of step 1 through Quadro Comil.
3. Materials of step 2 are transferred to Rapid Mixer Granulator and mixed for 20 minutes.
4. Povidone is dissolved in Isopropyl Alcohol by stirring.
5. Blend of step 3 is granulated using the binder solution of step 4.
6. Wet mass of step 5 is dried using Rapid Dryer.
7. Dried mass of step 6 is milled using Quadro Comil to form granules.
8. Magnesium Stearate is sifted through sieve #60 ASTM.
9. Granules of step 7 are blended with Magnesium Stearate of Step 8 using Octagonal Blender.
10. Blend of step 9 is compressed into tablets using respective tooling using Tablet Compression Machine.

In the composition described in Table 8, the mannitol is a filler, the povidone is a binder, the poloxamers are a surfactant, the hypromellose is a controlled-release agent, the silica colloidal anhydrous is a glidant, the ferric oxide NF is a colorant, and the magnesium stearate is a lubricant.

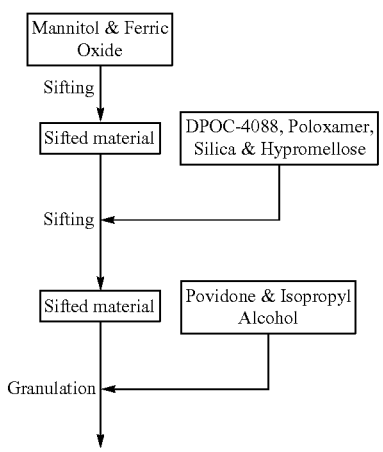

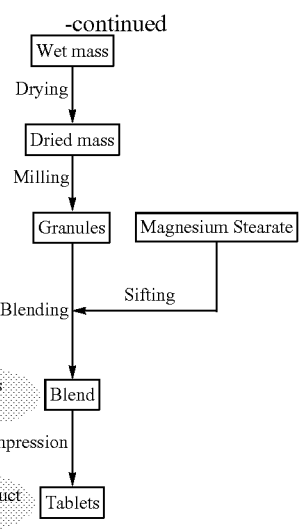

In Vitro Release Study

The compositions were tested for dissolution of DPOC-4088 in 900 ml of 0.1N HCl as dissolution medium at 37° C. using USP type II dissolution apparatus (with stationary basket) rotated at 50 rpm. The sampling was done at 0, 1, 2, 4, 6, 8, 10, 12, 14, 16, 20 and 24 hours. The results are tabulated as Table 9.

TABLE 9

| Time (hours) | % release of DPOC-4088 | | | |
|---|---|---|---|---|
| | Formulation A | Formulation B | Formulation C | Formulation D |
| 0 | 0.0 | 0.0 | 0.0 | 0.0 |
| 1 | 3.9 | 4.8 | 3.2 | 3.1 |
| 2 | 10.1 | 11.9 | 7.5 | 7.5 |
| 4 | 25.1 | 27.8 | 17.9 | 18.1 |
| 6 | 40.8 | 43.6 | 29.0 | 29.1 |
| 8 | 55.7 | 58.8 | 40.0 | 40.1 |
| 10 | 69.4 | 72.6 | 50.5 | 50.4 |
| 12 | 81.7 | 84.4 | 60.4 | 60.3 |
| 14 | 91.9 | 93.7 | 70.3 | 69.5 |
| 16 | 98.5 | 99.8 | 78.5 | 77.9 |
| 20 | 102.6 | 102.4 | 91.8 | 91.4 |
| 24 | 103.4 | 102.5 | 97.4 | 98.9 |

The rate of release of the active ingredient till the time until 90% of the active ingredient is released is tabulated as Tables 10 and 11. The rate of release of the active ingredient at the end of specified time point is calculated using the formula $(Q_2-Q_1)/(T_2-T_1)$, where $Q_2$ is the % release of the active ingredient at the end of specified time point and $Q_1$ is the % release of the active ingredient at the end preceding time point to the specified time point. $T_2$ & $T_1$ refer to specified time point and preceding time point respectively.

For example the rate of release of the active ingredient for formulation A at the end of 1 hour is calculated as follows $(3.9-0)/(1-0)=3.9$.

TABLE 10

Release rate of DPOC-4088
(Percent deviation from mean release rate)

| Time (hours) | Formulation A | Formulation B |
|---|---|---|
| 1 | 3.9 (39%) | 4.8 (27%) |
| 2 | 6.2 (3%) | 7.1 (8%) |
| 4 | 7.5 (17%) | 8.0 (21%) |
| 6 | 7.9 (23%) | 7.9 (20%) |
| 8 | 7.5 (17%) | 7.6 (15%) |
| 10 | 6.9 (8%) | 6.9 (5%) |
| 12 | 6.2 (3%) | 5.9 (11%) |
| 14 | 5.1 (20%) | 4.7 (29%) |
| Mean Release Rate | 6.4 | 6.6 |

TABLE 11

Release rate of DPOC-4088

| Time (hours) | Formulation C | Formulation D |
|---|---|---|
| 1 | 3.2 | 3.1 |
| 2 | 4.3 | 4.4 |
| 4 | 5.2 | 5.3 |
| 6 | 5.6 | 5.5 |
| 8 | 5.5 | 5.5 |
| 10 | 5.3 | 5.2 |
| 12 | 5.0 | 5.0 |
| 14 | 5.0 | 4.6 |
| 16 | 4.1 | 4.2 |
| 20 | 3.3 | 3.4 |
| Mean Release Rate | 4.6 | 4.6 |

As can be inferred from 10 and 11 above, the release rate till the time until 90% of the active ingredient is released (i.e. 16 hours for formulations A, B and 20 hours for formulations C and D) does not deviate by not more than 50% of the mean release rate of the active ingredient illustrating that the in vitro release of the active ingredient from the formulations is substantially constant. The percent deviation is calculated using the formula $(RT_{sp}-RT_m)/RT_m \times 100$ where $RT_m$ is the mean release rate of the active ingredient and $RT_{sp}$ is the mean release rate of the active ingredient at the specified time point. For example the mean release rate of the active ingredient for formulation C at the end of 1 hour is calculated as follows $(3.9-6.4)/6.4*100=-39\%$.

Formulation A and Formulation B containing 100 mg and 200 mg of DPOC-4088 were found to release at least 85% at the end of 16 hours (16 hour formulation) and Formulation C and Formulation D containing 100 mg and 200 mg DPOC-4088 were found to release at least 85% at the end of 24 hours (20 hour formulation).

Example 2

Four formulations having same composition as those described in Example 1 were dosed in a clinical study. The objective of this single dose, randomized, open-label, 4-period crossover study was to (1) compare plasma concentration-ratios and other standard PK parameters following single oral dosing with 100 mg and 200 mg DPOC-4088 tablets in two prolonged release formulations (16 and 20 hr); (2) determine the extent of thrombin inhibition of these formulations as measured by activated partial thromboplastin time [aPTT], ecarin clotting time [ECT], thrombin time [TT] and prothrombin time [PT] (reported as the international normalized ratio [INR]); (i.e. PD parameters) and (3) assess the safety of DPOC-4088 in healthy volunteers.

Twelve subjects aged 21 to 45 (mean 32.9±8.55) years were enrolled, and were dosed in 4 periods after an overnight fast and had blood drawn for PK/PD determinations immediately prior to dosing and at specified time intervals for 48 hrs post-dosing. Each dosing period was separated by a ≥5-day washout. The observed PK and PD parameters are tabulated as Table 12.

TABLE 12

PK/PD Parameters of Two Doses and Two Prolonged Release Formulations of DPOC-4088

| PK/PD Parameter[a] | 100 mg 16 hr formulation | 200 mg, 16 hr formulation | 100 mg, 20 hr formulation | 200 mg, 20 hr formulation |
|---|---|---|---|---|
| n | 12[b] | 12[c] | 12[d] | 12[e] |
| $C_{max}$, nM | 721 | 1497 | 572 | 1099 |
| Ratio $C_{max}/C_{12\ hr}$ | 2.6 | 2.9 | 2.2 | 2.6 |
| Ratio $C_{max}/C_{24\ hr}$ | 4.4 | 3.9 | 2.4 | 3.1 |
| $T_{max}$, hr (range) | 3.0 (2.0-6.0) | 3.0 (2.0-6.0) | 4.0 (3.0-24.0) | 3.0 (2.0-6.0) |
| $AUC_{0-\infty}$, nM · hr | 9652 | 20070 | 9243 | 15940 |
| $T_{1/2\ terminal}$, hr | 5.0 | 5.8 | 5.3 | 4.0 |
| aPTT, % max change | 28.7 | 39.2 | 24.1 | 35.1 |
| aPTT, % change at 24 hr | 12.3 | 24.1 | 15.0 | 21.0 |
| ECT, % max change | 49.8 | 76.6 | 40.7 | 69.6 |
| ECT, % change at 24 hr | 20.9 | 36.0 | 23.2 | 34.6 |

[a]Values presented as geometric mean;
$t_{max}$: median (range);
aPTT and ECT: % change in mean value compared to pre-dose.
For $AUC_{0-\infty}$ and $T_{1/2\ terminal}$:
[b]n = 11;
[c]n = 9;
[d]n = 9;
[e]n = 8.

In the clinical study the plasma levels achieved after oral dosing of the four extended release formulation containing DPOC-4088 is tabulated as Table 13.

TABLE 13

| | Plasma Concentration (nM) | | | |
|---|---|---|---|---|
| Time (hours) | 100 mg, 16 hr formulation | 200 mg, 16 hr formulation | 100 mg, 20 hr formulation | 200 mg 20 hr formulation |
| 0 | 0.00 | 0.00 | 0 | 0 |
| 1 | 341.29 | 479.10 | 244.5 | 490.3 |
| 2 | 587.00 | 940.83 | 440.4 | 810.6 |
| 3 | 666.50 | 1361.17 | 475.8 | 957.7 |
| 4 | 617.17 | 1265.67 | 490.3 | 1025 |
| 6 | 610.00 | 1065.83 | 498.7 | 923.1 |
| 8 | 398.67 | 764.00 | 279.8 | 558.9 |
| 12 | 299.92 | 584.08 | 276.3 | 475.4 |
| 14 | 301.75 | 536.67 | 294.1 | 502.3 |
| 16 | 228.87 | 431.69 | 230.5 | 442.4 |
| 18 | 179.00 | 349.36 | 191.3 | 336.8 |
| 20 | 155.07 | 299.37 | 197.1 | 299.8 |
| 24 | 236.82 | 452.13 | 274.4 | 430.2 |
| 32 | 68.60 | 219.76 | 107.2 | 242.8 |
| 48 | 12.00 | 63.59 | 23.59 | 67.41 |

The plasma levels of the formulations are diagrammatically represented in FIGS. 6-9. As illustrated by these figures, the extended releases formulations containing DPOC-4088 did not exhibit any significant peaks illustrating that substantially constant plasma levels are achieved from the extended release formulations after oral administration. A plasma level of 200 nM is maintained for at least about 16 hours (Table 14) evidencing the constant plasma levels of DPOC-4088 achieved from the extended release formulation. The $C_{max}/C_{24}$ values (the numerical expression of degree of fluctuation) of the extended release formulations are less than 8 (Table 13), further demonstrating the constant plasma levels of DPOC-4088 from the extended release formulations.

Increases in Cmax and AUC were dose proportional for both formulations, with the 20 hr-release formulation exhibiting slightly lower $C_{max}$, and $C_{max}/C_{12\ hr}$ and $C_{max}/C_{24\ hr}$ ratios for a given dose compared to the 16 hr formulation (Table). Median $t_{max}$ was 3-4 hrs. Geometric means of terminal elimination half-life ($T_{1/2\ terminal}$) ranged from 4.0 to 5.8 hrs.

At 24 hrs post-dose, mean aPTT remained 12-15% above the pre-dose aPTT after 100 mg DPOC-4088 and 21-24% above pre-dose after 200 mg. The mean 24 hr ECT remained 21-23% and 35-36% above the pre-dose ECT for the 100 and 200 mg doses, respectively.

Mean TT versus time curves for all four treatments combined are shown in FIG. 12. A clear, dose dependent increase in TT was observed after administration of DPOC-4088, for both formulations, with mean values still above baseline at 24 hrs post-dose. Based on the statistical analyses, the maximum change in TT was 1.46 times (16 hr formulation) and 1.38 times (20 hr formulation) higher for the 200 mg dose compared to the 100 mg dose. The maximum change in TT was slightly higher for the 16 hr formulation compared to the 20 hr formulation. For the 100 mg dose level the mean maximum fold change from baseline was 2.34 for the 16 hr formulation and 2.10 for the 20 hr formulation. For the 200 mg dose level the mean maximum fold changes were 3.43 and 2.96, respectively. For the 200 mg dose level this difference was statistically significant (p-value below 0.05), while for the 100 mg dose level this was not the case (p-value 0.0586).

Compared to pre-dose values, increases in all pharmacodynamic clotting parameters (aPTT, ECT, TT, and INR) closely followed the shape of the PK profile, were dose-dependent, and exhibited no lag time in response, suggesting a direct effect of DPOC-4088 (Table 12).

TABLE 14

PD Parameters of Two Doses and Two Extended Release Formulations of DPOC-4088

| PD Parameter[a] | 100 mg, 16 hr | 200 mg, 16 hr | 100 mg, 20 hr | 200 mg, 20 hr |
|---|---|---|---|---|
| n | 12[b] | 12[c] | 12[d] | 12[e] |
| aPTT, % max change | 28.7 | 39.2 | 24.1 | 35.1 |
| aPTT, % change at 24 hr | 12.3 | 24.1 | 15.0 | 21.0 |
| ECT, % max change | 49.8 | 76.6 | 40.7 | 69.6 |
| ECT, % change at 24 hr | 20.9 | 36.0 | 23.2 | 34.6 |

[a]aPTT and ECT: % change in mean value compared to pre-dose.

Figure 11A:
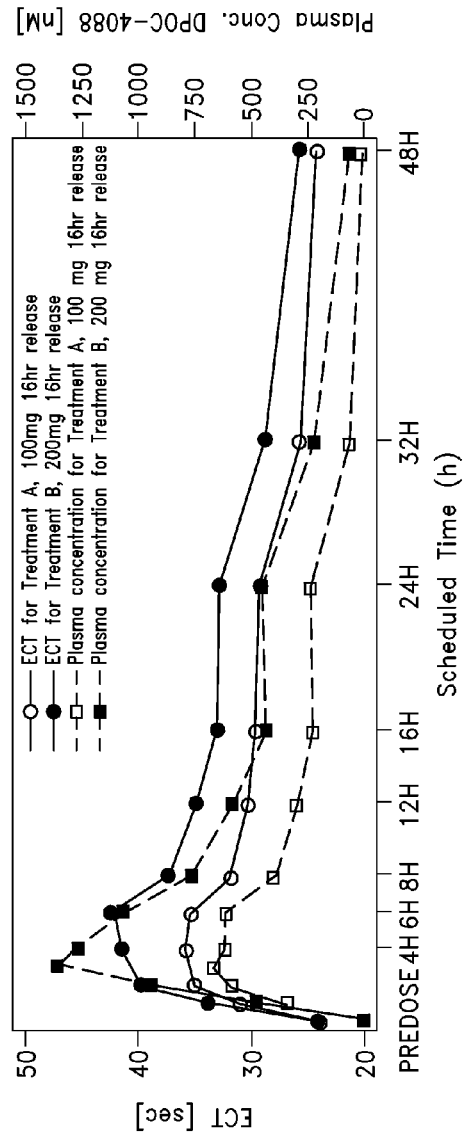
FIG. 11a is a diagram showing mean ECT Versus Time Curves After Administration of a Single Dose of 100 or 200 mg DPOC-4088 Formulated as a 16 hr Prolonged Release Formulation.
Figure 11B:
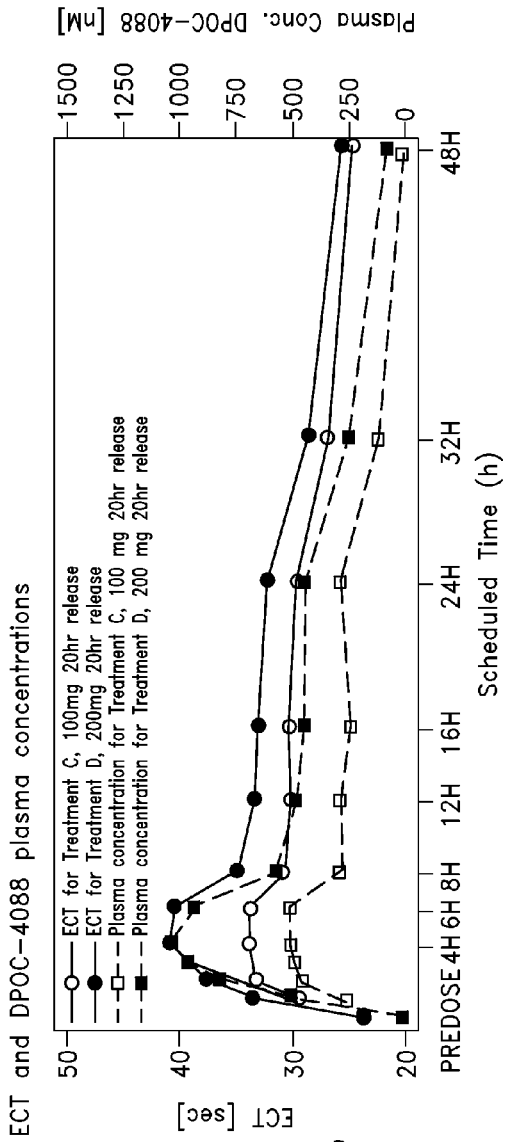
FIG. 11b is a diagram showing mean ECT Versus Time Curves After Administration of a Single Dose of 100 or 200 mg DPOC-4088 Formulated as a 20 hr Prolonged Release Formulation.
Figures 13A, 13B:
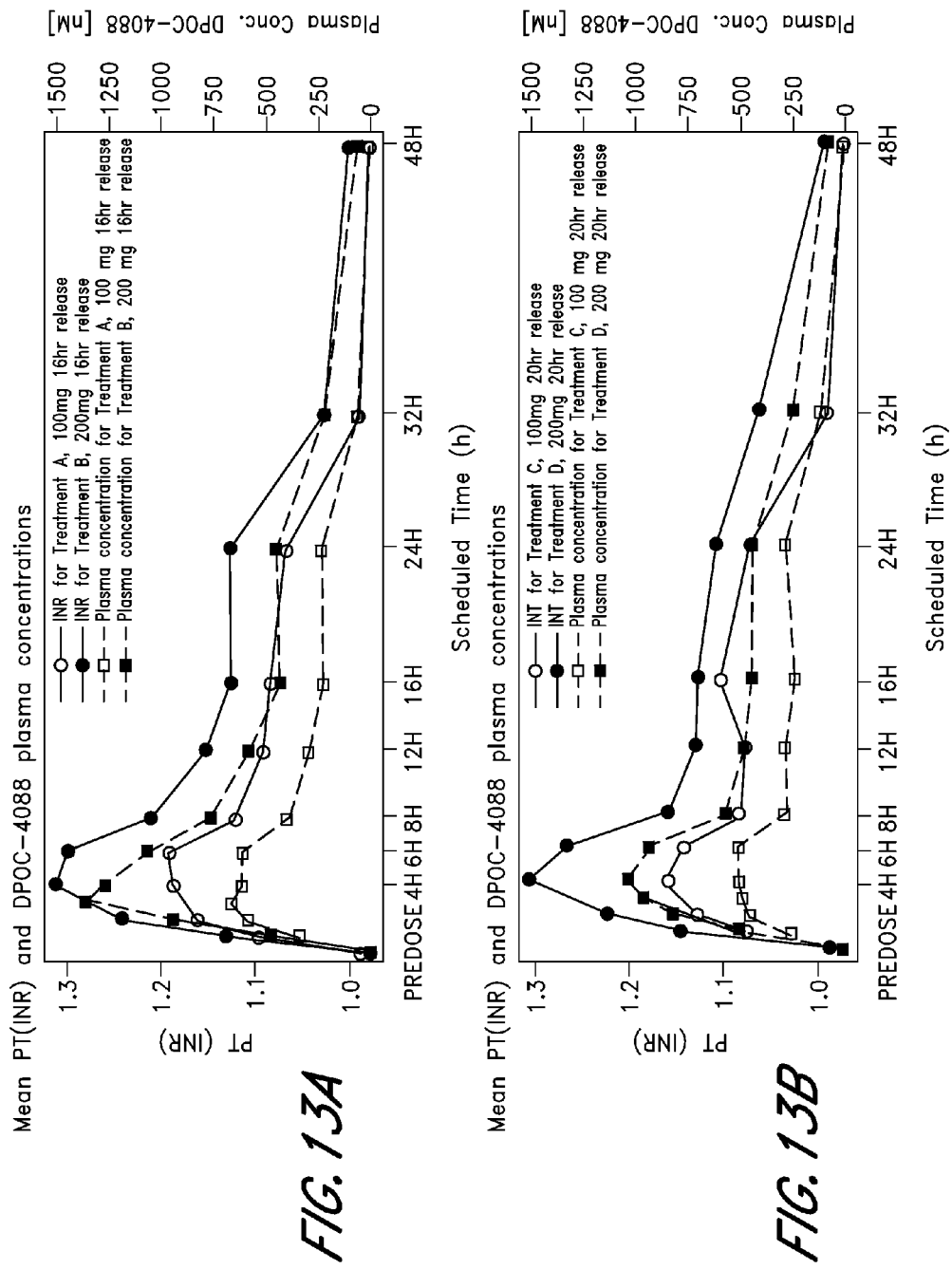
FIG. 13 is a graph showing Mean PT (INR) Versus Time Curves After Administration of a Single Dose of 100 or 200 mg DPOC-4088 Formulated as a 16 hr or 20 hr Prolonged Release Formulation.

Changes in aPTT (FIGS. 10a-b), ECT (FIGS. 11a-b), TT (FIGS. 12a-b), and PT (INR) (FIGS. 13a-b) were well-correlated with peak DPOC-4088 concentrations. The mean INR versus time curves for all four treatments combined are shown in FIGS. 13a-b. A dose dependent increase in INR was observed after dosing, with mean values still above baseline levels at 24 hrs post-dose. Based on the statistical analyses, the maximum change in INR was 1.13 times (16 hr formulation) and 1.11 times (20 hr formulation) higher for the 200 mg dose compared to the 100 mg dose. The mean INR versus time profiles for the 16 hr and 20 hr formulations were very similar and also the maximum change compared to pre-dose was virtually the same for both formulations. For the 100 mg dose level the mean maximum fold change from baseline was 1.24 for the 16 hr formulation and 1.22 for the 20 hr formulation. For the 200 mg dose level the mean maximum fold changes from baseline were 1.40 and 1.36, respectively. As for the other coagulation parameters, mean INR versus time curves followed the shape of the mean DPOC-4088 PK curves closely.

Evidence of anticoagulation efficacy by direct thrombin inhibition was reflected in key PD clotting parameters. Mean TT returned to within 1-15% of pre-dosing TT by 48 hrs. After single doses of 100 or 200 mg DPOC-4088, mean peak INRs were reached at 4 hrs for both the 100 mg (1.15-1.17) and 200 mg (1.28-1.30) formulations, returning to pre-dose INRs by 48 hrs. DPOC-4088 at both doses and release formulations was well-tolerated. Adverse events (AEs) occurred in 9/12 subjects; most were grade 1, unrelated or unlikely to be related to DPOC-4088, and resolved within hours without sequelae (headache, oropharyngeal pain, nausea, cervical lymphadenopathy, neck pain, fatigue). Among the AEs considered at least possibly related to DPOC-4088 administration, only grade 1 epistaxis (n=1) and blood in stools (n=1) were potentially linked to the PD activity of DPOC-4088. At 100 and 200 mg doses, DPOC-4088 was safe and well-tolerated.

Example 3

Randomized, double-blind, placebo-controlled, stepwise study of the pharmacokinetics (PK), pharmacodynamics (PD), PK/PD characteristics and safety of multiple once-daily oral dosing of DPOC-4088 in healthy young male subjects
Preliminary Safety, PK, and PD Results Dose Step 1: 100 mg q.d.
Safety
10 healthy volunteers participated in the first step of the multiple dose study (8 received DPOC-4088 and 2 received placebo). No treatment emergent serious adverse events (AEs) were reported. Minor AEs were reported. All AEs were grade 1, transient and were resolved. No bruising (except for puncture site hematomas) or petechiae were reported and the physical (including neurological) exams were normal in all volunteers. The lab exams were within normal limits or deviating without clinical significance. All safety data indicated that DPOC-4088 at the 100 mg level is very safe after 10 days of oral administration.

Pharmacokinetics

Figure 14A:
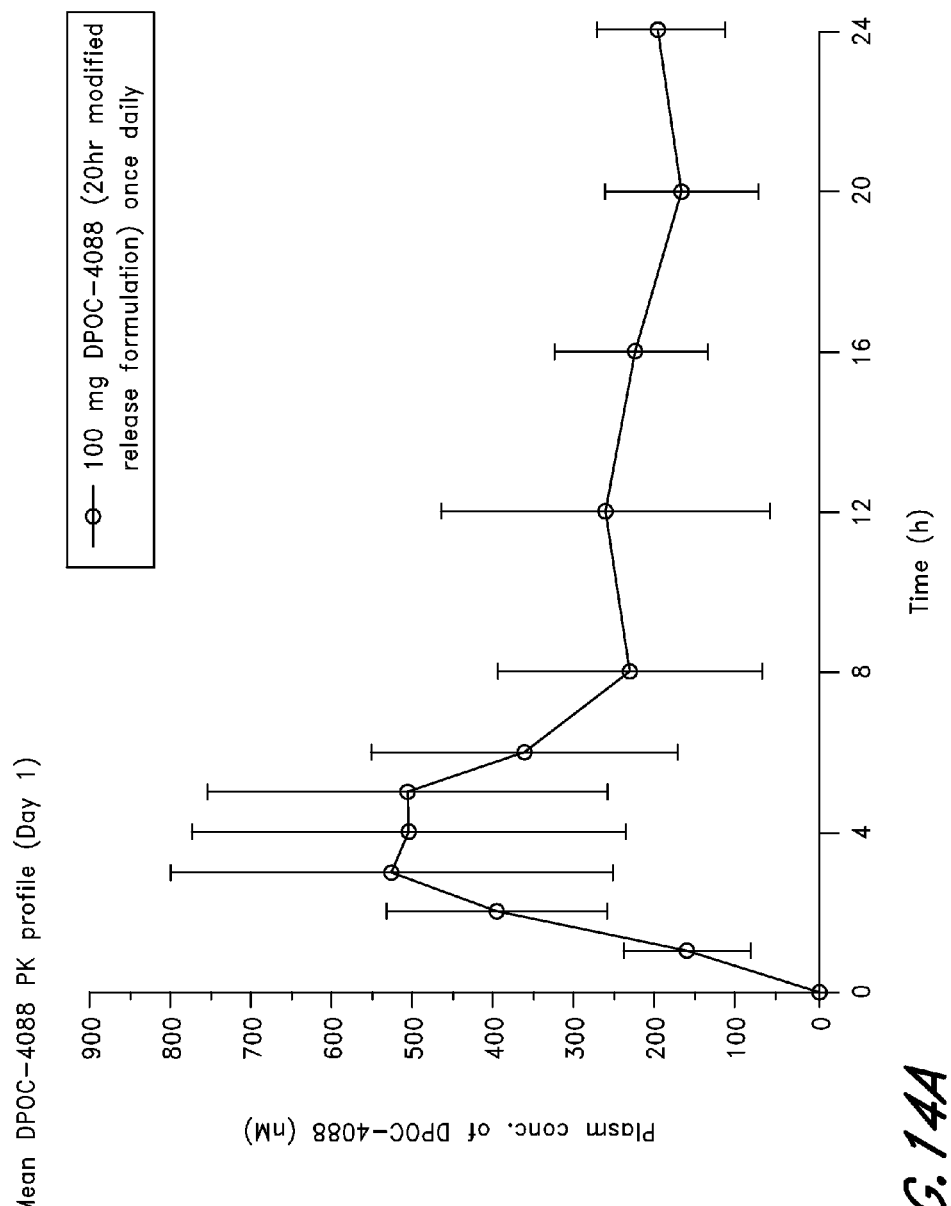
FIG. 14a is a graph showing the mean DPOC-4088 pharmacokinetic profile at day 1 of a 100 mg dose (20 hr modified release formulation) administered daily.
Figure 14B:
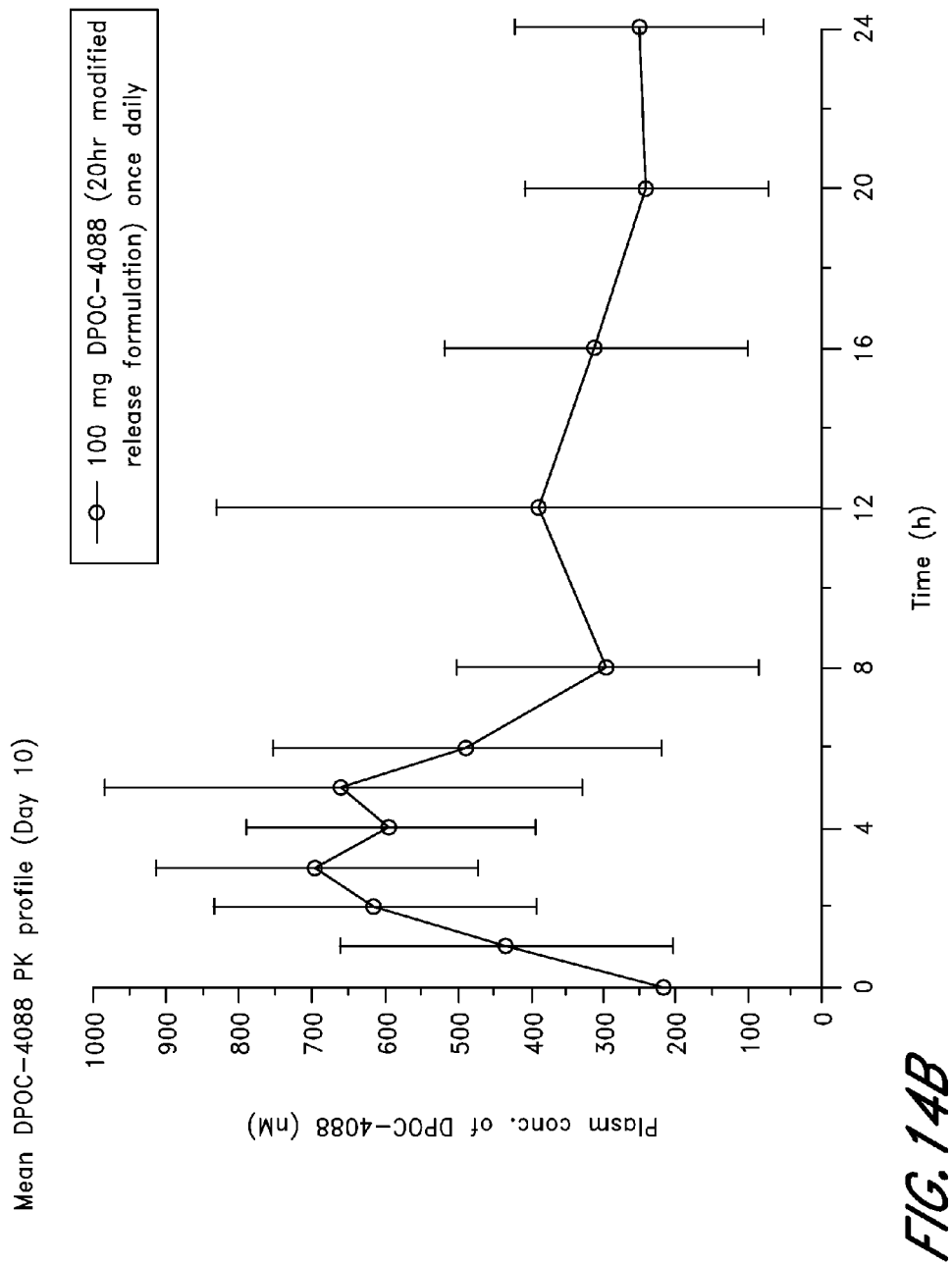
FIG. 14b is a graph showing the mean DPOC-4088 pharmacokinetic profile at day 10 of a 100 mg dose (20 hr modified release formulation) administered daily.

A summary of calculated PK parameters, including trough (predose) levels on Day 2 to 10 is provided in Table 10. Mean PK profiles of DPOC-4088 on Day 1 (first dose) and Day 10 (steady-state) are shown in FIGS. 14 a-b, respectively.

- On Day 1, the mean PK profile was in line with observation from the previous single dose study (DPOC-001).
- The degree of accumulation to steady-state levels was modest with a Day 10/Day 1 ratio for $AUC_{24h}$ of 1.4. This value was consistent with the value predicted based on data from Study DPOC-001, suggesting no apparent time dependent effects in DPOC-4088 pharmacokinetics.
- Between subject variability in trough (predose) levels of DPOC-4088 on Day 3-10 was fairly high and individual subjects showed day-to-day fluctuations with respect to these levels. Between subject variability in maximum plasma levels on Day 10 was modest (% CV 38%).
- For this dose level $t_{1/2}$ could not be determined as plasma levels decreased quickly during washout (indicating a short half-life) resulting in insufficient sampling time points during the elimination phase with plasma levels above the limit of quantification to allow for reliable determination of $t_{1/2}$.

Pharmacodynamics

Figure 15A:
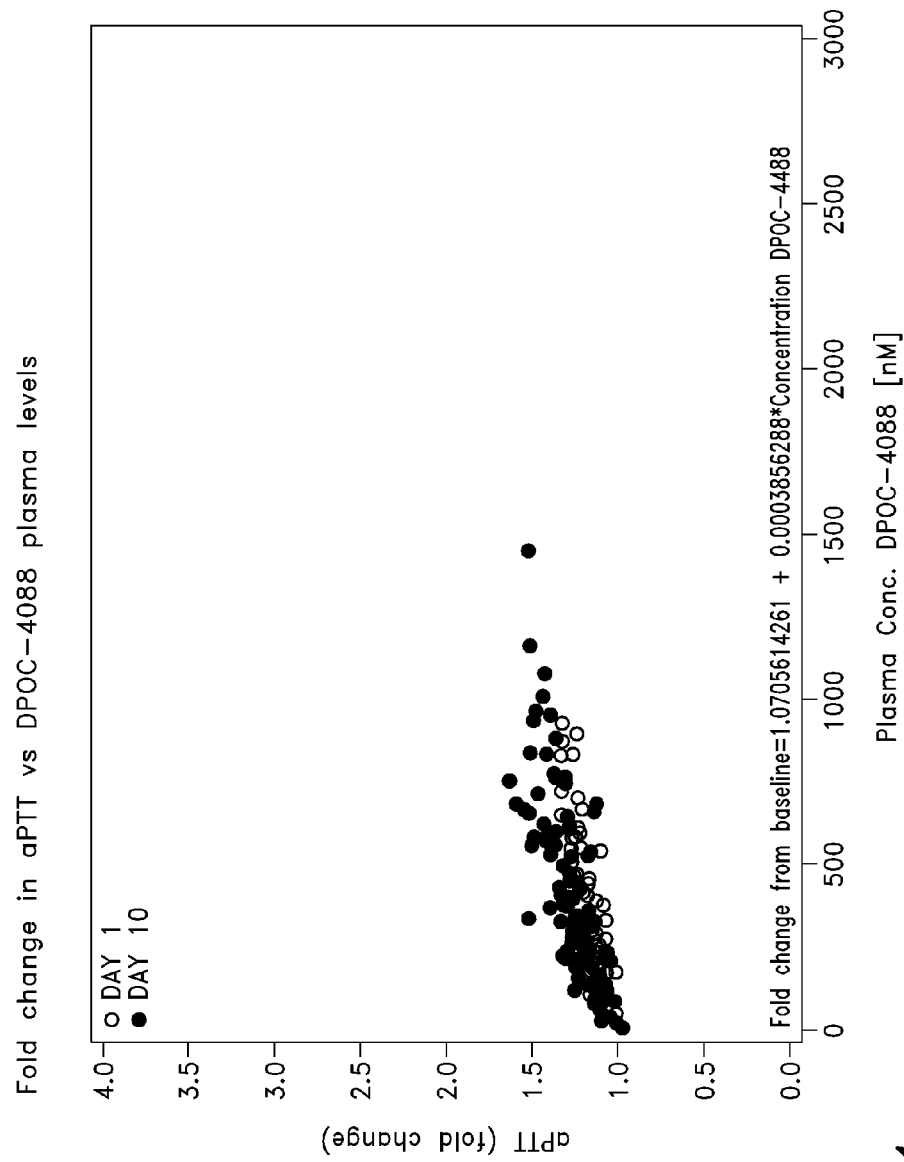
FIG. 15a is a graph showing the fold change in aPTT vs. DPOC-4088 plasma levels.
Figure 15B:
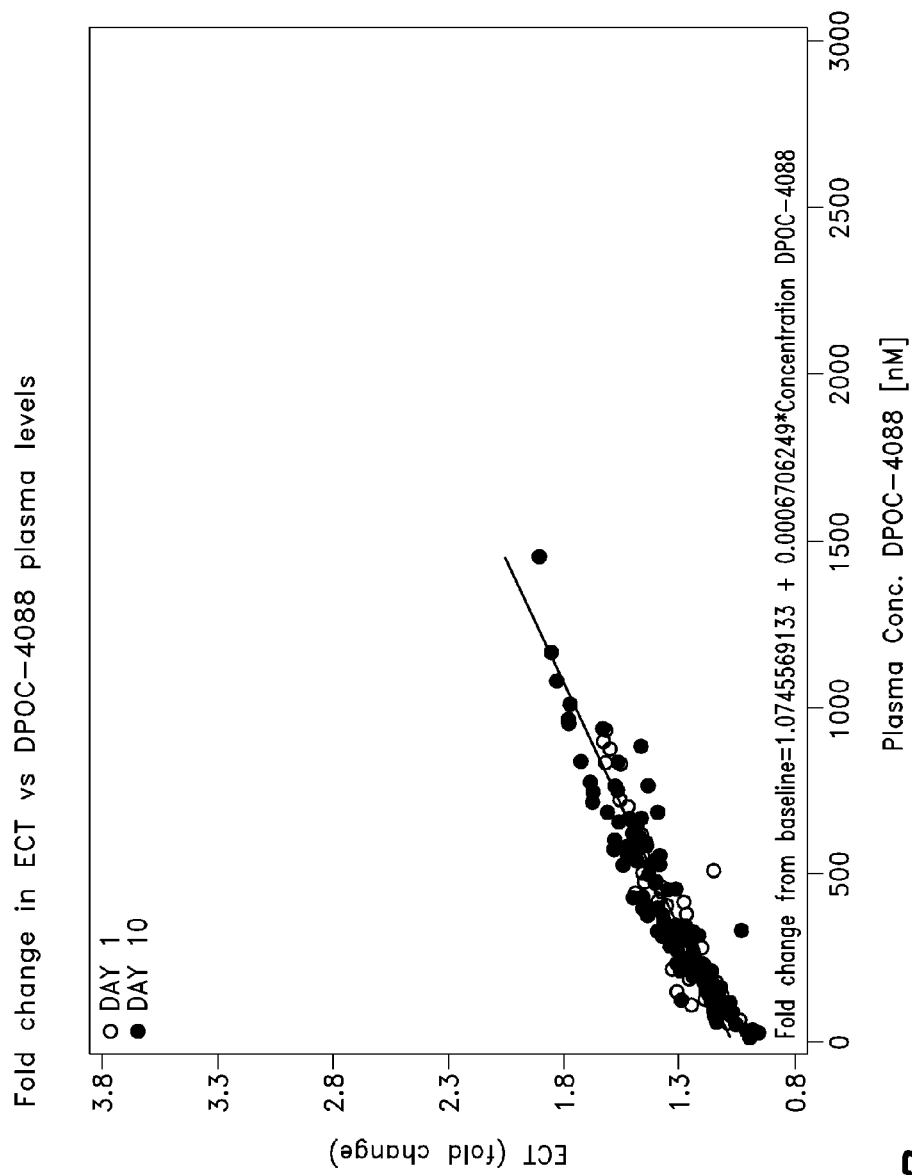
FIG. 15b is a graph showing the fold change in ECT vs. DPOC-4088 plasma levels.

Mean maximum and minimum fold changes compared to baseline (Day 1, pre dose) in ECT, aPTT and PT on Day 10 are shown in Table 15. Scatter plots of fold changes in aPTT and ECT versus DPOC-4088 plasma levels are shown in FIGS. 15a-b, respectively.

- Changes in coagulation parameters over time closely followed changes in DPOC-4088 plasma levels, suggesting a direct effect, as was also observed previously in the single dose study (DPOC-001).
- Maximum fold changes in ECT and aPTT compared to baseline on Day 10 were 1.64 and 1.49 respectively. Minimum changes in ECT and aPTT on Day 10 were 1.12 and 1.10 respectively (Table 16). These values are lower than the target values defined in the protocol which were 2 and 1.5, respectively, at steady-state trough levels (see below).
- Linear regression on the changes in ECT and aPTT versus DPOC-4088 plasma levels was performed. The results suggested a linear relationship for both ECT and aPTT versus the available DPOC-4088 plasma levels.
- For dabigatran, another direct thrombin inhibitor, a linear relationship between ECT and plasma levels has been reported. This was also shown for aPTT but this relationship levels off at higher concentrations (van Ryn et. al. Thromb Haemost. 2010 June; 103(6):1116-27. Epub 2010 Mar. 29.).
- Based on the PK data on Day 10 of the first step of the multiple dose study, assuming dose linearity, for daily doses of 200 or 300 mg of DPOC-4088, maximum DPOC-4088 levels can be expected to be in the range of 2000 nM and 3000 nM respectively (observed geometric mean value for 100 mg is approximately 800 nM).
- For these maximum levels, based on the regression analyses, for aPTT 1.8 fold and 2.2 fold changes from baseline would be expected on Day 10 for 200 mg and 300 mg once daily respectively. For ECT the changes would be 2.4 and 3.1 fold respectively.
- For reference, for dabigatran, clinically relevant doses result in changes in aPTT of approximately 1.50 fold at trough levels and 2-fold at maximum levels. For ECT these changes are approximately 2-fold at trough levels and 3-fold at maximum levels.

TABLE 15

| PK parameters of DPOC-4088 Pharmacokinetics of DPOC-4088 (geometric mean, mean ± SD, $t_{max}$: median [range]) | 100 mg DPOC-4088 (20 hr modified release formulation) once daily | |
|---|---|---|
| n | 8 | |
| Day 1 | | |
| $C_{max}$, nM | 551.1 | 596.3 ± 242.5 |
| $t_{max}$, h | — | 4.0 (2.0-24.0) |
| $AUC_{0-24\ h}$, nM · h | 5888 | 6366 ± 2644 |
| Day 2 | | |
| $C_{0\ h}$, nM | 177.1 | 197.4 ± 78.85 |
| Day 3 | | |
| $C_{0\ h}$, nM | 207.1 | 258.6 ± 161.2 |
| Day 4 | | |
| $C_{0\ h}$, nM | 118.5 | 179.8 ± 195.0 |
| Day 5 | | |
| $C_{0\ h}$, nM | 120.5 | 169.6 ± 112.0 |
| Day 7 | | |
| $C_{0\ h}$, nM | 301.9 | 326.8 ± 140.4 |
| Day 9 | | |
| $C_{0\ h}$, nM | 310.0 | 341.5 ± 155.8 |
| Day 10 | | |
| $C_{0\ h}$, nM | 142.6 | 218.9 ± 174.7 |
| $C_{min-ss}$, nM | 87.27 | 115.7 ± 82.47 |
| $C_{max-ss}$, nM | 811.1 | 870.8 ± 332.8 |
| $t_{max}$, h | — | 4.0 (2.0-12.0) |
| $AUC_{0-24\ h}$, nM · h | 7975 | 8888 ± 4046 |
| $C_{ss-av}$, nM | 332.3 | 370.3 ± 168.6 |
| $\lambda_z$, 1/h | — | — |
| $t_{1/2term}$, h | — | — |
| Ratio $C_{max-ss}/C_{min-ss}$ | 9.295 | 15.11 ± 17.27 |
| Ratio $AUC_{0-24\ h}$ Day 10/Day 1 | 1.354 | 1.456 ± 0.6741 |

TABLE 16

Mean fold-changes compared to baseline in aPTT, ECT and PT on Day 10

| mean fold change | max | min |
|---|---|---|
| aPTT | 1.49 | 1.10 |
| ECT | 1.64 | 1.12 |
| PT (INR) | 1.39 | 1.12 |

The new extended release formulations of DPOC-4088 improve the bioavailability of the active substance during its transit through the gut and provide an acceptable safety profile when used in the intended clinical setting. The correlation between PK and key PD parameters (aPTT and ECT) at the 100 and 200 mg doses was superior to that of the drilled tablet formulations. This improved PK/PD correlation provides a more predictable pharmacologic effect on clotting parameters at a given dose, and translate into an improved safety profile and ease of dose titration.

Compared to pre-dose values, increases in all PD clotting parameters (aPTT, ECT, TT, and INR) closely followed the shape of the PK profile, were dose-dependent, and exhibited no lag time in response, suggesting a direct effect of DPOC-4088. Changes in aPTT, ECT, TT, and PT (INR) were well-correlated with peak DPOC-4088 concentrations. Anticoagulation efficacy shown by direct thrombin inhibition was reflected in key PD clotting parameters. The PD parameters were well-correlated with DPOC-4088 plasma concentrations and other PK parameters. At 100 and 200 mg doses, DPOC-4088 was safe and well-tolerated.

What is claimed is:

1. A method for providing a therapeutic blood plasma concentration of 3-fluoro-2-pyridylmethyl-3-(2,2-difluoro-2-(2-pyridyl)ethylamino)-6-chloropyrazin-2-one-1-acetamide (DPOC-4088) over a twenty four hour period which comprises administering orally to a patient in need thereof an extended release formulation comprising an effective amount of DPOC-4088 that provides a blood plasma concentration of DPOC-4088 of greater than 200 nM/100 mg of DPOC-4088 administered over a period of at least about 16 hours following a single oral dose, wherein the extended release formulation comprises a tablet core comprising the DPOC-4088 and a matrix forming polymer configured to modulate a release of the DPOC-4088 from the tablet core comprises:
   100.00 mg DPOC-4088;
   27.375 mg manitol;
   15.00 mg povidone;
   25.00 mg poloxamers;
   60.00 mg hypromellose;
   2.50 mg colloidal anhydrous silica;
   0.25 mg ferric oxide; and
   2.375 mg magnesium stearate.

2. The method of claim 1 wherein the period is at least about 18 hours.

3. The method of claim 1, wherein the extended release formulation further comprises a surfactant and other conventional pharmaceutical excipients.

4. A method for providing a therapeutic blood plasma concentration of 3-fluoro-2-pyridylmethyl-3-(2,2-difluoro-2-(2-pyridyl)ethylamino)-6-chloropyrazin-2-one-1-acetamide (DPOC-4088) over a twenty four hour period which comprises administering orally to a patient in need thereof an extended release formulation comprising an effective amount of DPOC-4088 that provides a blood plasma concentration of DPOC-4088 of greater than 200 nM/100 mg of DPOC-4088 administered over a period of at least about 16 hours following a single oral dose, wherein the extended release formulation comprises a tablet core comprising the DPOC-4088 and a matrix forming polymer configured to modulate a release of the DPOC-4088 from the tablet core, wherein the extended release formulation provides a blood plasma concentration of DPOC-4088 of greater than 200 nM/100 mg of DPOC-4088 administered over a period of 18 hours following a single oral dose, and wherein the tablet core comprises:
   200.00 mg DPOC-4088;
   69.75 mg manitol;
   30.00 mg povidone;
   50.00 mg poloxamers;
   75.00 mg hypromellose;
   5.00 mg colloidal anhydrous silica;
   0.50 mg ferric oxide; and
   4.75 mg magnesium stearate.

5. A method for providing a therapeutic blood plasma concentration of 3-fluoro-2-pyridylmethyl-3-(2,2-difluoro-2-(2-pyridyl)ethylamino)-6-chloropyrazin-2-one-1-acetamide (DPOC-4088) over a twenty four hour period which comprises administering orally to a patient in need thereof an extended release formulation comprising an effective amount of DPOC-4088 that provides a blood plasma concentration of DPOC-4088 of greater than 200 nM/100 mg of DPOC-4088 administered over a period of at least about 16 hours following a single oral dose, wherein the extended release formulation comprises a tablet core comprising the DPOC-4088 and a matrix forming polymer configured to modulate a release of the DPOC-4088 from the tablet core, wherein the extended release formulation provides a blood plasma concentration of DPOC-4088 of greater than 200 nM/100 mg of DPOC-4088 administered over a period of 20 hours following a single oral dose, and wherein the tablet core comprises:
   100.00 mg DPOC-4088;
   17.5 mg manitol;
   15.00 mg povidone;
   25.00 mg poloxamers;
   90.00 mg hypromellose;
   2.50 mg colloidal anhydrous silica;
   0.50 mg ferric oxide; and
   2.50 mg magnesium stearate.

6. A method for providing a therapeutic blood plasma concentration of 3-fluoro-2-pyridylmethyl-3-(2,2-difluoro-2-(2-pyridyl)ethylamino)-6-chloropyrazin-2-one-1-acetamide (DPOC-4088) over a twenty four hour period which comprises administering orally to a patient in need thereof an extended release formulation comprising an effective amount of DPOC-4088 that provides a blood plasma concentration of DPOC-4088 of greater than 200 nM/100 mg of DPOC-4088 administered over a period of at least about 16 hours following a single oral dose, wherein the extended release formulation comprises a tablet core comprising the DPOC-4088 and a matrix forming polymer configured to modulate a release of the DPOC-4088 from the tablet core, wherein the extended release formulation provides a blood plasma concentration of DPOC-4088 of greater than 200 nM/100 mg of DPOC-4088 administered over a period of 20 hours following a single oral dose, and wherein the tablet core comprises:
   200.00 mg DPOC-4088;
   54.75 mg manitol;
   30.00 mg povidone;
   50.00 mg poloxamers;
   120.00 mg hypromellose;
   5.00 mg colloidal anhydrous silica;
   0.50 mg ferric oxide; and
   4.75 mg magnesium stearate.

7. The method of claim 1, wherein the therapeutic blood plasma concentration of DPOC-4088 is provided to treat a thromboembolism in the patient in need thereof.

8. The method of claim 1, wherein the matrix forming polymer comprises from about 10% to about 50% by weight of the extended release formulation.

* * * * *